(12) United States Patent
Liu et al.

(10) Patent No.: US 11,242,371 B2
(45) Date of Patent: *Feb. 8, 2022

(54) FUSION POLYPEPTIDES AND METHODS OF USE

(71) Applicant: Prosit Sole Biotechnology (Beijing) Co. Ltd, Beijing (CN)

(72) Inventors: Hongyu Liu, Beijing (CN); Mingzhi Zhao, Beijing (CN); Hetong Sun, Beijing (CN)

(73) Assignee: Prosit Sole Biotechnology (Beijing) Co, Ltd, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/252,530

(22) Filed: Jan. 18, 2019

(65) Prior Publication Data

US 2019/0382461 A1 Dec. 19, 2019

Related U.S. Application Data

(63) Continuation of application No. 15/107,101, filed as application No. PCT/CN2014/070328 on Jan. 8, 2014, now Pat. No. 10,246,501.

(51) Int. Cl.
*C07K 14/54* (2006.01)
*C07K 14/555* (2006.01)
*A61K 38/00* (2006.01)
*A61K 38/21* (2006.01)

(52) U.S. Cl.
CPC ............ *C07K 14/54* (2013.01); *C07K 14/555* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,500,707 A | 2/1985 | Caruthers et al. | |
| 5,436,327 A | 7/1995 | Southern et al. | |
| 5,700,637 A | 12/1997 | Southern | |
| 7,157,559 B2 * | 1/2007 | Brady ................... | A61P 29/00 530/351 |
| 7,655,223 B2 | 2/2010 | Sheppard et al. | |
| 7,655,233 B2 | 2/2010 | Van et al. | |
| 8,759,027 B2 | 6/2014 | Zamost et al. | |
| 8,980,245 B2 | 3/2015 | Ho | |
| 9,089,535 B2 | 7/2015 | Davies et al. | |
| 10,246,501 B2 | 4/2019 | Liu et al. | |
| 2010/0222552 A1 | 9/2010 | Zamost et al. | |
| 2011/0263484 A1 | 10/2011 | Moore et al. | |
| 2014/0349294 A1 | 11/2014 | Church et al. | |
| 2017/0022259 A1 | 1/2017 | Liu et al. | |

FOREIGN PATENT DOCUMENTS

| | | |
|---|---|---|
| CN | 101031316 A | 9/2007 |
| CN | 101918440 A | 12/2010 |
| JP | 2007528719 A | 10/2007 |
| JP | 2008508310 A | 3/2008 |
| JP | 2008522600 A | 7/2008 |
| JP | 2009510173 A | 3/2009 |
| JP | 2010538662 A | 12/2010 |
| JP | 2017503505 A | 2/2017 |
| JP | 6730926 B2 | 7/2020 |
| WO | WO-9739127 A1 | 10/1997 |
| WO | WO-9852976 A1 | 11/1998 |
| WO | WO-0003317 A1 | 1/2000 |
| WO | WO-02079232 A2 | 10/2002 |
| WO | WO-2006012644 A2 | 2/2006 |
| WO | WO-2009036510 A1 | 3/2009 |
| WO | WO-2015103749 A1 | 7/2015 |

OTHER PUBLICATIONS

Kolchanov, 1988, Journal of Molecular Evolution, vol. 27, pp. 154-162; (Year: 1988).*
Pasquo, 2012, PLoS ONE, vol. 7, Issue 2, e32555). (Year: 2012).*
Bork, 2000, Genome Research 10:398-400; (Year: 2000).*
Bork et al., 1996, Trends in Genetics 12:425-427 (Year: 1996).*
Yu et al. Design and evaluation of novel interferon lambda analogs with enhanced antiviral activity and improved drug attributes. Drug Design, Development and Therapy 10:163-182 (Jan. 1, 2016).
Ank, et al. Lambda interferon (IFN-lambda), a type III IFN, is induced by viruses and IFNs and displays potent antiviral activity against select virus infections in vivo. J Virol. May 2006;80(9):4501-9.
Ausubel, et al., Current Protocols in molecular biology. Greene publishing and association and Wiley-interscience. 1987.
Bitter et al. Expression and secretion vectors for yeast. Methods Enzymol 153:516-544 (1987).
Bork, et al., Go hunting in sequence databases but watch out for the traps. Trends in Genetics 1996; 12:425-427.
Bork, P., Powers and pitfalls in Sequence analysis: The 70% hurdle. Genome Research 2000; 10:398-400.
Brown, et al., The crystal structure of fibroblast growth factor 18 (FGF18). Protein Cell. 2014. 5(5):343-347.
Cespedes, et al. Mouse models in oncogenesis and cancer therapy. Clin Transl Oncol. May 2006;8(5):318-29.
Coccia, et al. Viral infection and Toll-like receptor agonists induce a differential expression of type I and lambda interferons in human plasmacytoid and monocyte-derived dendritic cells. Eur J Immunol. Mar. 2004;34(3):796-805.

(Continued)

Primary Examiner — Gary B Nickol
Assistant Examiner — Jegatheesan Seharaseyon
(74) Attorney, Agent, or Firm — Wilson Sonsini Goodrich & Rosati

(57) ABSTRACT

Disclosed are fusion polypeptides comprising fragments from a first and a second isoform of an interferon lambda family, nucleic acids encoding the fusion polypeptides, and vectors and host cells containing the same, and methods of making and using such compositions in treatment of interferon lambda-related diseases, disorders, and conditions.

24 Claims, 17 Drawing Sheets

Specification includes a Sequence Listing.

(56) References Cited

OTHER PUBLICATIONS

Cunningham, et al. Efficacy and safety of telaprevir in patients with genotype 1 hepatitis C infection. Therap Adv Gastroenterol. Mar. 2012;5(2):139-51. doi: 10.1177/1756283X11426895.

D'Abbadie, et al., Molecular breeding of polymerases for amplification of ancient DNA. Nat Biotechnol. Aug. 2007; 25(8): 939-943.

Doyle, et al. Interleukin-29 uses a type 1 interferon-like program to promote antiviral responses in human hepatocytes. Hepatology. Oct. 2006;44(4):896-906.

EBI. EMBOSS Needle. Available at http://www.ebi.ac.uk/Tools/psa/emboss_needle/. Accessed on Dec. 20, 2016.

Ellman, et al., Biological impact of the fibroblast growth factor family on articular cartilage and intervertebral disc homeostasis (basic FGF, FGF-18, osteoarthritis, IVD degeneration). Gene. Aug. 2008; 420(1):82-89.

Ellsworth, Jet al., Fibroblast growth factor-18 is a trophic factor for mature chondrocytes and their progenitors. Osteoarthritis and Cartilage (2002) 10, 308-320.

European Search Report dated May 26, 2017 for EP Application No. 14877922.6.

Farran, et al., Enhanced Integration with Treatment of Sprifermin (rhFGF18) in a Cartilage Injury-Repair Model. UPO Journal. 2014.

Fidler, et al., Direct antiproliferative effects of recombinant human interferon—a B/D Hybrids on human tumor cell lines. Cancer Research, Apr. 15, 1987; 47:2020-2027.

Fortier, et al., The role of growth factors in cartilage repair. Clin orthop Relat Res. 2011;469:2706-2715.

Getgood, et al., Osteochondral tissue engineering using a biphasic collagen/GAG scaffold containing rhFGF18 or BMP-7 in an ovine model. Journal of Experimental Orthopaedics 2014, 1:13.

Hopp, et al., Prediction of protein antigenic determinants from amino acid sequences. PNAS. Jun. 1981; 78(1):3824-3828.

Horisberger, at al., Interferon-alpha hybrids. Pharmacol Ther. Jun. 1995;66(3):507-34.

International search report and written opinion dated Oct. 10, 2014 for PCT/CN2014/070328.

Kerbel, et al. Human tumor xenografts as predictive preclinical models for anticancer drug activity in humans: better than commonly perceived—but they can be improved. Cancer Biol Ther. Jul.-Aug. 2003;2(4 Suppl 1):S134-9.

Kolchanov, et al., Single amino acid substitutions producing instability of globular proteins calculation of their frequencies in the entire mutational spectra of the a- and B-subunits of human hemoglobin. Journal of Molecular Evolution, 1988; vol. 27, pp. 154-162.

Kotenko, et al. IFN-lambdas mediate antiviral protection through a distinct class II cytokine receptor complex. Nat Immunol. Jan. 2003;4(1):69-77. Epub Dec. 16, 2002.

Levitt, M. A simplified representation of protein conformations for rapid simulation of protein folding. Journal of Molecular Biology. Jun. 1976; 104(1): 59-107.

Liu, et al., FGF18 is required for early chondrocyte proliferation, hypertrophy and vascular invasion of the growth plate. Developmental Biology 302 (2007) 80-91.

Lohmander, et al., Intraarticular Sprifermin (Recombinant Human Fibroblast Growth Factor 18) in Knee Osteoarthritis: A Randomized, Double-Blind, Placebo-Controlled Trial. Arthritis & Rheumatology. Jul. 2014; 66(7):1820-1831.

Man, et al. On the development of models in mice of advanced visceral metastatic disease for anti-cancer drug testing. Cancer Metastasis Rev. Dec. 2007;26(3-4):737-47.

Marcello, et al. Interferons alpha and lambda inhibit hepatitis C virus replication with distinct signal transduction and gene regulation kinetics. Gastroenterology. Dec. 2006;131(6):1887-98. Epub Oct. 1, 2006.

Matteucci, et al. The synthesis of oligodeoxyprimidines on a polymer support. Tetrahedron Letters. 1980; 21(8):719-722.

Mcpherson, et al. A Randomized, Double-Blind, Placebo-Controlled, Multicenter Study of RHFGF18 Administered Intraarticularly Using Single or Multiple Ascending Doses in Patients With Primary Knee Osteoarthritis (OA), not Expected to Require Knee Surgery Within 1 Year. Oral Presentations / Osteoarthritis and Cartilage 19S1 (2011) S7-S52.

Meager, et al. Biological activity of interleukins-28 and -29: comparison with type I interferons. Cytokine. Jul. 21, 2005;31(2):109-18.

Miller, et al. Interferon lambda as a potential new therapeutic for hepatitis C. Ann N Y Acad Sci. Dec. 2009;1182:80-7. doi: 10.1111/j.1749-6632.2009.05241.x.

Moore, et al., Fibroblast growth factor-18 stimulates chondrogenesis and cartilage repair in a rat model of injury-induced osteoarthritis. OsteoArthritis and Cartilage (2005) 13, 623-631.

Needleman, et al., A general method applicable to the search for similarities in the amino acid sequence of two proteins. Journal of Molecular Biology. Mar. 1970; 48(3):443-453.

Notice of allowance dated Dec. 21, 2018 for U.S. Appl. No. 15/107,101.

Pasquo, et al., Structural stability of human protein tyrosine phosphatase p Catalytic domain: Effect of point mutations. Plos One, 2000; 7(2), e32555.

Power, et al., Intra-articular injection of rhfgf-18 improves the healing in microfracture treated chondral defects in an ovine model. Journal of orthopaedic research. Jan. 2014.

Robek, et al. Lambda interferon inhibits hepatitis B and C virus replication. J Virol. Mar. 2005;79(6):3851-4.

Sambrook, et al., Molecular cloning: A laboratory manual. Cold spring harbor laboratory press. 1989.

Shepherd, et al. Pegylated interferon alpha-2a and -2b in combination with ribavirin in the treatment of chronic hepatitis C: a systematic review and economic evaluation. Health Technol Assess. Oct. 2004;8(39):iii-iv, 1-125.

Sheppard, et al. IL-28, IL-29 and their class II cytokine receptor IL-28R. Nat Immunol. Jan. 2003;4(1):63-8. Epub Dec. 2, 2002.

Shimoaka, et al., Regulation of Osteoblast, Chondrocyte, and Osteoclast Functions by Fibroblast Growth Factor (FGF)-18 in Comparison with FGF-2 and FGF-10*. The journal of biological chemistry. vol. 277, No. 9, Issue of Mar. 1, pp. 7493-7500, 2002.

Stickler, et al. Human population-based identification of CD4(+) T-cell peptide epitope determinants. J Immunol Methods. Oct. 1, 2003;281(1-2):95-108.

Sturniolo, T. et al., Generation of tissue-specific and promiscuous HLA ligand databases using DNA microarrays and virtual HLA class II matrices. Nat. Biotech. 17 (1999): 555-561.

Talmadge, et al. Murine models to evaluate novel and conventional therapeutic strategies for cancer. Am J Pathol. Mar. 2007;170(3):793-804.

U.S. Appl. No. 15/107,101 Office Action dated Apr. 20, 2018.

Zhang, et al., Fibroblast growth factor 18 increases the trophic effects of bone marrow mesenchymal stem cells on chondrocytes isolated from late stage osteoarthritic patients. Hindawi. Aug. 2014; 8 pages.

Zhang, et al., Receptor Specificity of the Fibroblast Growth Factor Family, Part II. The American society for biochemistry and molecular biology. Apr. 2006.1-16.

Hamming, et al. Lambda Interferons: New Cytokines with Old Functions. Pharmaceuticals (Basel). Apr. 2010; 3(4): 795-809. Published online Mar. 25, 2010. doi: 10.3390/ph3040795.

* cited by examiner

Cloning and expression of SEQ ID NO: 8

Cloning and expression of SEQ ID NO: 12

Refolding and purification of SEQ ID NO: 8

Refolding and purification of SEQ ID NO: 12

Compound A: N-terminal PEGylated SEQ ID NO: 3, Compound B: N-terminal PEGylated SEQ ID NO: 5,
Compound C: N-terminal PEGylated SEQ ID NO: 7, Compound D: N-terminal PEGylated SEQ ID NO: 11,
Compound E: N-terminal PEGylated SEQ ID NO: 12, Compound F: N-terminal PEGylated SEQ ID NO: 13.

Compound G: SEQ ID NO 14 PEGylated at C168, Compound H: SEQ ID NO 15 PEGylated at C168.

SEQ ID NO: 1, SEQ ID NO: 12, SEQ ID NO: 3, SEQ ID NO: 16, and SEQ ID NO: 17 at 10ng/ml,
PEGylated SEQ ID NO: 16 and PEGylated SEQ ID NO:17 at 100ng/ml,
12h after induction SEQ ID NO: 1, SEQ ID NO: 12, SEQ ID NO: 3, SEQ ID NO: 16, and SEQ ID NO: 17 at 10ng/ml, pegylated SEQ ID NO: 16 and pegylated SEQ ID NO:17 at 100ng/ml, 12h after induction Figure on the right is a numerical summary of Figure on the left

|   | SEQ ID NO: 16 | | | SEQ ID NO: 17 | | | SEQ ID NO: 1 | | | | | |
|---|---|---|---|---|---|---|---|---|---|---|---|---|
|   | 1 | 2 | 3 | 4 | 5 | 6 | 7 | 8 | 9 | 10 | 11 | 12 |
| A | 500ng/ml | 500ng/ml | 500ng/ml | 500ng/ml | 500ng/ml | 500ng/ml | 500ng/ml | 500ng/ml | 500ng/ml | | CV | |
| B | 50ng/ml | 50ng/ml | 50ng/ml | 50ng/ml | 50ng/ml | 50ng/ml | 50ng/ml | 50ng/ml | 50ng/ml | | | |
| C | 5ng/ml | 5ng/ml | 5ng/ml | 5ng/ml | 5ng/ml | 5ng/ml | 5ng/ml | 5ng/ml | 5ng/ml | | | |
| D | 0.5ng/ml | 0.5ng/ml | 0.5ng/ml | 0.5ng/ml | 0.5ng/ml | 0.5ng/ml | 0.5ng/ml | 0.5ng/ml | 0.5ng/ml | | | |
| E | 500ng/ml | 500ng/ml | 500ng/ml | 500ng/ml | 500ng/ml | 500ng/ml | 500ng/ml | 500ng/ml | 500ng/ml | | VV | |
| F | 50ng/ml | 50ng/ml | 50ng/ml | 50ng/ml | 50ng/ml | 50ng/ml | 50ng/ml | 50ng/ml | 50ng/ml | | | |
| G | 5ng/ml | 5ng/ml | 5ng/ml | 5ng/ml | 5ng/ml | 5ng/ml | 5ng/ml | 5ng/ml | 5ng/ml | | | |
| H | 0.5ng/ml | 0.5ng/ml | 0.5ng/ml | 0.5ng/ml | 0.5ng/ml | 0.5ng/ml | 0.5ng/ml | 0.5ng/ml | 0.5ng/ml | | | |
|   | PEG-NO: 16 | | | PEG-NO: 17 | | | IFN a2b | | | | | |

*Fig. 16*

SEQUENCE LISTING

<160> NUMBER OF SEQ IDS: 19

<210> SEQ ID NO 1
<211> LENGTH: 176
<212> TYPE: PRT
<213> ORGANISM: Homo sapiens

<400> SEQUENCE: 1

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr

```
                    85                  90                  95

Leu His His Ile Leu Ser Gln Leu Gln Ala Cys Ile Gln Pro Gln Pro
                100                 105                 110

Thr Ala Gly Pro Arg Pro Arg Gly Arg Leu His His Trp Leu His Arg
            115                 120                 125

Leu Gln Glu Ala Pro Lys Lys Glu Ser Ala Gly Cys Leu Glu Ala Ser
        130                 135                 140

Val Thr Phe Asn Leu Phe Arg Leu Leu Thr Arg Asp Leu Lys Tyr Val
145                 150                 155                 160

Ala Asp Gly Asn Leu Ser Leu Arg Thr Ser Thr His Pro Glu Ser Thr
                165                 170                 175

<210> SEQ ID NO 2
<211> LENGTH: 176
<212> TYPE: PRT
<213> ORGANISM: Homo sapiens

<400> SEQUENCE: 2

Met Val Pro Val Ala Arg Leu Arg Gly Ala Leu Pro Asp Ala Arg Gly
1               5                   10                  15

Cys His Ile Ala Gln Phe Lys Ser Leu Ser Pro Gln Glu Leu Gln Ala
            20                  25                  30

Phe Lys Arg Ala Lys Asp Ala Leu Glu Glu Ser Leu Leu Leu Lys Asp
        35                  40                  45

Ser Lys Cys Arg Ser Arg Leu Phe Pro Arg Thr Trp Asp Leu Arg Gln
    50                  55                  60

Leu Gln Val Arg Glu Arg Pro Val Ala Leu Glu Ala Glu Leu Ala Leu
65                  70                  75                  80

Thr Leu Lys Val Leu Glu Ala Thr Ala Asp Thr Asp Pro Ala Leu Gly
                85                  90                  95

Asp Val Leu Asp Gln Pro Leu His Thr Leu His His Ile Leu Ser Gln
                100                 105                 110

Leu Arg Ala Cys Ile Gln Pro Gln Pro Thr Ala Gly Pro Arg Thr Arg
            115                 120                 125

Gly Arg Leu His His Trp Leu His Arg Leu Gln Glu Ala Pro Lys Lys
        130                 135                 140

Glu Ser Pro Gly Cys Leu Glu Ala Ser Val Thr Phe Asn Leu Phe Arg
145                 150                 155                 160

Leu Leu Thr Arg Asp Leu Asn Ser Val Ala Ser Gly Asp Leu Ser Val
                165                 170                 175

<210> SEQ ID NO 3
<211> LENGTH: 169
<212> TYPE: PRT
<213> ORGANISM: Artificial Sequence
<220> FEATURE:
<223> OTHER INFORMATION: fusion polypeptides

<400> SEQUENCE: 3

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60
```

```
Val Ala Leu Glu Ala Glu Leu Ala Leu Thr Leu Lys Val Leu Glu Ala
 65                  70                  75                  80

Thr Ala Asp Thr Asp Pro Ala Leu Gly Asp Val Leu Asp Gln Pro Leu
                 85                  90                  95

His Thr Leu His His Ile Leu Ser Gln Leu Arg Ala Cys Ile Gln Pro
            100                 105                 110

Gln Pro Thr Ala Gly Pro Arg Thr Gly Arg Leu His His Trp Leu
        115                 120                 125

His Arg Leu Gln Glu Ala Pro Lys Lys Glu Ser Pro Gly Cys Leu Glu
130                 135                 140

Ala Ser Val Thr Phe Asn Leu Phe Arg Leu Leu Thr Arg Asp Leu Asn
145                 150                 155                 160

Ser Val Ala Ser Gly Asp Leu Ser Val
                165
```

<210> SEQ ID NO 4
<211> LENGTH: 183
<212> TYPE: PRT
<213> ORGANISM: Artificial Sequence
<220> FEATURE:
<223> OTHER INFORMATION: FUSION POLYPEPTIDES

<400> SEQUENCE: 4

```
Met Val Pro Val Ala Arg Leu Arg Gly Ala Leu Pro Asp Ala Arg Gly
  1               5                  10                  15

Cys His Ile Ala Gln Phe Lys Ser Leu Ser Pro Gln Glu Leu Gln Ala
             20                  25                  30

Phe Lys Arg Ala Lys Asp Ala Leu Glu Glu Ser Leu Leu Leu Lys Asp
         35                  40                  45

Ser Lys Cys Arg Ser Arg Leu Phe Pro Arg Thr Trp Asp Leu Arg Gln
 50                  55                  60

Leu Gln Val Arg Glu Arg Pro Val Ala Leu Glu Ala Glu Leu Ala Leu
 65                  70                  75                  80

Thr Leu Lys Val Leu Glu Ala Ala Gly Pro Ala Leu Glu Asp Val
                 85                  90                  95

Leu Asp Gln Pro Leu His Thr Leu His His Ile Leu Ser Gln Leu Gln
                100                 105                 110

Ala Cys Ile Gln Pro Gln Pro Thr Ala Gly Pro Arg Pro Arg Gly Arg
            115                 120                 125

Leu His His Trp Leu His Arg Leu Gln Glu Ala Pro Lys Lys Glu Ser
        130                 135                 140

Ala Gly Cys Leu Glu Ala Ser Val Thr Phe Asn Leu Phe Arg Leu Leu
145                 150                 155                 160

Thr Arg Asp Leu Lys Tyr Val Ala Asp Gly Asn Leu Ser Leu Arg Thr
                165                 170                 175

Ser Thr His Pro Glu Ser Thr
                180
```

<210> SEQ ID NO 5
<211> LENGTH: 167
<212> TYPE: PRT
<213> ORGANISM: Artificial Sequence
<220> FEATURE:
<223> OTHER INFORMATION: fusion polypeptide

<400> SEQUENCE: 5

Met Lys Pro Thr Thr Thr Gly Lys Gly Cys His Ile Gly Arg Phe Lys

-continued

```
              1               5                  10                 15
            Ser Leu Ser Pro Gln Glu Leu Ala Ser Phe Lys Lys Ala Arg Asp Ala
                            20                 25                 30
            Leu Glu Glu Ser Leu Lys Leu Lys Asn Trp Ser Cys Ser Ser Pro Val
                            35                 40                 45
            Phe Pro Gly Asn Trp Asp Leu Arg Leu Leu Gln Val Arg Glu Arg Pro
                50                            55                 60
            Val Ala Leu Glu Ala Glu Leu Ala Leu Thr Leu Lys Val Leu Glu Ala
             65                 70                 75                 80
            Ala Ala Gly Pro Ala Leu Glu Asp Val Leu Asp Gln Pro Leu His Thr
                            85                 90                 95
            Leu His His Ile Leu Ser Gln Leu Arg Ala Cys Ile Gln Pro Gln Pro
                            100                105                110
            Thr Ala Gly Pro Arg Thr Arg Gly Arg Leu His Trp Leu His Arg
                            115                120                125
            Leu Gln Glu Ala Pro Lys Lys Glu Ser Pro Gly Cys Leu Glu Ala Ser
                            130                135                140
            Val Thr Phe Asn Leu Phe Arg Leu Leu Thr Arg Asp Leu Asn Ser Val
            145                150                155                160
            Ala Ser Gly Asp Leu Ser Val
                            165

<210> SEQ ID NO 6
<211> LENGTH: 185
<212> TYPE: PRT
<213> ORGANISM: Artificial Sequence
<220> FEATURE:
<223> OTHER INFORMATION: FUSION POLYPEPTIDES

<400> SEQUENCE: 6

Met Val Pro Val Ala Arg Leu Arg Gly Ala Leu Pro Asp Ala Arg Gly
  1               5                  10                 15
Cys His Ile Ala Gln Phe Lys Ser Leu Ser Pro Gln Glu Leu Gln Ala
                20                 25                 30
Phe Lys Arg Ala Lys Asp Ala Leu Glu Glu Ser Leu Leu Leu Lys Asp
                35                 40                 45
Ser Lys Cys Arg Ser Arg Leu Phe Pro Arg Thr Trp Asp Leu Arg Gln
 50                            55                 60
Leu Gln Val Arg Glu Arg Pro Val Ala Leu Glu Ala Glu Leu Ala Leu
 65                 70                 75                 80
Thr Leu Lys Val Leu Glu Ala Thr Ala Asp Thr Asp Pro Ala Leu Gly
                85                 90                 95
Asp Val Leu Asp Gln Pro Leu His Thr Leu His Ile Leu Ser Gln
                100                105                110
Leu Gln Ala Cys Ile Gln Pro Gln Pro Thr Ala Gly Pro Arg Pro Arg
                115                120                125
Gly Arg Leu His His Trp Leu His Arg Leu Gln Glu Ala Pro Lys Lys
                130                135                140
Glu Ser Ala Gly Cys Leu Glu Ala Ser Val Thr Phe Asn Leu Phe Arg
145                150                155                160
Leu Leu Thr Arg Asp Leu Lys Tyr Val Ala Asp Gly Asn Leu Ser Leu
                165                170                175
Arg Thr Ser Thr His Pro Glu Ser Thr
                180                185
```

-continued

```
<210> SEQ ID NO 7
<211> LENGTH: 167
<212> TYPE: PRT
<213> ORGANISM: Artificial Sequence
<220> FEATURE:
<223> OTHER INFORMATION: FUSION POLYPEPTIDES

<400> SEQUENCE: 7

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Pro Gly Cys Leu Glu Ala Ser
    130                 135                 140

Val Thr Phe Asn Leu Phe Arg Leu Leu Thr Arg Asp Leu Asn Ser Val
145                 150                 155                 160

Ala Ser Gly Asp Leu Ser Val
                165

<210> SEQ ID NO 8
<211> LENGTH: 185
<212> TYPE: PRT
<213> ORGANISM: Artificial Sequence
<220> FEATURE:
<223> OTHER INFORMATION: FUSION POLYPEPTIDES

<400> SEQUENCE: 8

Met Val Pro Val Ala Arg Leu Arg Gly Ala Leu Pro Asp Ala Arg Gly
1               5                   10                  15

Cys His Ile Ala Gln Phe Lys Ser Leu Ser Pro Gln Glu Leu Gln Ala
            20                  25                  30

Phe Lys Arg Ala Lys Asp Ala Leu Glu Glu Ser Leu Leu Leu Lys Asp
        35                  40                  45

Ser Lys Cys Arg Ser Arg Leu Phe Pro Arg Thr Trp Asp Leu Arg Gln
    50                  55                  60

Leu Gln Val Arg Glu Arg Pro Val Ala Leu Glu Ala Glu Leu Ala Leu
65                  70                  75                  80

Thr Leu Lys Val Leu Glu Ala Thr Ala Asp Thr Pro Ala Leu Gly
                85                  90                  95

Asp Val Leu Asp Gln Pro Leu His Thr Leu His His Ile Leu Ser Gln
            100                 105                 110

Leu Arg Ala Cys Ile Gln Pro Gln Pro Thr Ala Gly Pro Arg Thr Arg
        115                 120                 125

Gly Arg Leu His His Trp Leu His Arg Leu Gln Glu Ala Pro Lys Lys
    130                 135                 140
```

Glu Ser Ala Gly Cys Leu Glu Ala Ser Val Thr Phe Asn Leu Phe Arg
145                 150                 155                 160

Leu Leu Thr Arg Asp Leu Lys Tyr Val Ala Asp Gly Asn Leu Ser Leu
                165                 170                 175

Arg Thr Ser Thr His Pro Glu Ser Thr
                180                 185

<210> SEQ ID NO 9
<211> LENGTH: 167
<212> TYPE: PRT
<213> ORGANISM: Artificial Sequence
<220> FEATURE:
<223> OTHER INFORMATION: FUSION POLYPEPTIDES

<400> SEQUENCE: 9

Met Lys Pro Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
                20                  25                  30

Leu Glu Glu Ser Leu Lys Leu Lys Asn Trp Ser Cys Ser Ser Pro Val
            35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Asn Ser Val
145                 150                 155                 160

Ala Ser Gly Asp Leu Ser Val
                165

<210> SEQ ID NO 10
<211> LENGTH: 185
<212> TYPE: PRT
<213> ORGANISM: Artificial Sequence
<220> FEATURE:
<223> OTHER INFORMATION: FUSION POLYPEPTIDES

<400> SEQUENCE: 10

Met Val Pro Val Ala Arg Leu Arg Gly Ala Leu Pro Asp Ala Arg Gly
1               5                   10                  15

Cys His Ile Ala Gln Phe Lys Ser Leu Ser Pro Gln Glu Leu Gln Ala
                20                  25                  30

Phe Lys Arg Ala Lys Asp Ala Leu Glu Glu Ser Leu Leu Leu Lys Asp
            35                  40                  45

Ser Lys Cys Arg Ser Arg Leu Phe Pro Arg Thr Trp Asp Leu Arg Gln
        50                  55                  60

Leu Gln Val Arg Glu Arg Pro Val Ala Leu Glu Ala Glu Leu Ala Leu
65                  70                  75                  80

Thr Leu Lys Val Leu Glu Ala Thr Ala Asp Thr Asp Pro Ala Leu Gly
                85                  90                  95

Asp Val Leu Asp Gln Pro Leu His Thr Leu His His Ile Leu Ser Gln
            100                 105                 110

Leu Arg Ala Cys Ile Gln Pro Gln Pro Thr Ala Gly Pro Arg Thr Arg
            115                 120                 125

Gly Arg Leu His His Trp Leu His Arg Leu Gln Glu Ala Pro Lys Lys
130                 135                 140

Glu Ser Pro Gly Cys Leu Glu Ala Ser Val Thr Phe Asn Leu Phe Arg
145                 150                 155                 160

Leu Leu Thr Arg Asp Leu Lys Tyr Val Ala Asp Gly Asn Leu Ser Leu
                165                 170                 175

Arg Thr Ser Thr His Pro Glu Ser Thr
            180                 185

<210> SEQ ID NO 11
<211> LENGTH: 167
<212> TYPE: PRT
<213> ORGANISM: Artificial Sequence
<220> FEATURE:
<223> OTHER INFORMATION: FUSION POLYPEPTIDES

<400> SEQUENCE: 11

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Thr Arg Gly Arg Leu His His Trp Leu His Arg
            115                 120                 125

Leu Gln Glu Ala Pro Lys Lys Glu Ser Pro Gly Cys Leu Glu Ala Ser
        130                 135                 140

Val Thr Phe Asn Leu Phe Arg Leu Leu Thr Arg Asp Leu Asn Ser Val
145                 150                 155                 160

Ala Ser Gly Asp Leu Ser Val
                165

<210> SEQ ID NO 12
<211> LENGTH: 178
<212> TYPE: PRT
<213> ORGANISM: Artificial Sequence
<220> FEATURE:
<223> OTHER INFORMATION: FUSION POLYPEPTIDES

<400> SEQUENCE: 12

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val

```
                35                  40                  45

Phe Pro Gly Asn Trp Asp Leu Arg Leu Leu Gln Val Arg Glu Arg Pro
 50                  55                  60

Val Ala Leu Glu Ala Glu Leu Ala Leu Thr Leu Lys Val Leu Glu Ala
 65                  70                  75                  80

Thr Ala Asp Thr Asp Pro Ala Leu Gly Asp Val Leu Asp Gln Pro Leu
                 85                  90                  95

His Thr Leu His His Ile Leu Ser Gln Leu Arg Ala Cys Ile Gln Pro
            100                 105                 110

Gln Pro Thr Ala Gly Pro Arg Thr Gly Arg Leu His His Trp Leu
            115                 120                 125

His Arg Leu Gln Glu Ala Pro Lys Lys Glu Ser Ala Gly Cys Leu Glu
130                 135                 140

Ala Ser Val Thr Phe Asn Leu Phe Arg Leu Leu Thr Arg Asp Leu Lys
145                 150                 155                 160

Tyr Val Ala Asp Gly Asn Leu Ser Leu Arg Thr Ser Thr His Pro Glu
                165                 170                 175

Ser Thr

<210> SEQ ID NO 13
<211> LENGTH: 178
<212> TYPE: PRT
<213> ORGANISM: Artificial Sequence
<220> FEATURE:
<223> OTHER INFORMATION: FUSION POLYPEPTIDES

<400> SEQUENCE: 13

Met Lys Pro Thr Thr Thr Gly Lys Gly Cys His Ile Gly Arg Phe Lys
 1               5                  10                  15

Ser Leu Ser Pro Gln Glu Leu Ala Ser Phe Lys Lys Ala Arg Asp Ala
             20                  25                  30

Leu Glu Glu Ser Leu Lys Leu Lys Asn Trp Ser Cys Ser Ser Pro Val
         35                  40                  45

Phe Pro Gly Asn Trp Asp Leu Arg Leu Leu Gln Val Arg Glu Arg Pro
 50                  55                  60

Val Ala Leu Glu Ala Glu Leu Ala Leu Thr Leu Lys Val Leu Glu Ala
 65                  70                  75                  80

Thr Ala Asp Thr Asp Pro Ala Leu Gly Asp Val Leu Asp Gln Pro Leu
                 85                  90                  95

His Thr Leu His His Ile Leu Ser Gln Leu Arg Ala Cys Ile Gln Pro
            100                 105                 110

Gln Pro Thr Ala Gly Pro Arg Thr Gly Arg Leu His His Trp Leu
            115                 120                 125

His Arg Leu Gln Glu Ala Pro Lys Lys Glu Ser Pro Gly Cys Leu Glu
130                 135                 140

Ala Ser Val Thr Phe Asn Leu Phe Arg Leu Leu Thr Arg Asp Leu Lys
145                 150                 155                 160

Tyr Val Ala Asp Gly Asn Leu Ser Leu Arg Thr Ser Thr His Pro Glu
                165                 170                 175

Ser Thr

<210> SEQ ID NO 14
<211> LENGTH: 178
<212> TYPE: PRT
<213> ORGANISM: Artificial Sequence
<220> FEATURE:
```

<223> OTHER INFORMATION: FUSION POLYPEPTIDES

<400> SEQUENCE: 14

```
Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Thr Ala Asp Thr Asp Pro Ala Leu Gly Asp Val Leu Asp Gln Pro Leu
                85                  90                  95

His Thr Leu His His Ile Leu Ser Gln Leu Arg Ala Cys Ile Gln Pro
            100                 105                 110

Gln Pro Thr Ala Gly Pro Arg Thr Arg Gly Arg Leu His His Trp Leu
        115                 120                 125

His Arg Leu Gln Glu Ala Pro Lys Lys Glu Ser Ala Gly Cys Leu Glu
    130                 135                 140

Ala Ser Val Thr Phe Asn Leu Phe Arg Leu Leu Thr Arg Asp Leu Lys
145                 150                 155                 160

Tyr Val Ala Asp Gly Asn Leu Cys Leu Arg Thr Ser Thr His Pro Glu
                165                 170                 175

Ser Thr
```

<210> SEQ ID NO 15
<211> LENGTH: 178
<212> TYPE: PRT
<213> ORGANISM: Artificial Sequence
<220> FEATURE:
<223> OTHER INFORMATION: FUSION POLYPEPTIDES

<400> SEQUENCE: 15

```
Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Thr Ala Asp Thr Asp Pro Ala Leu Gly Asp Val Leu Asp Gln Pro Leu
                85                  90                  95

His Thr Leu His His Ile Leu Ser Gln Leu Arg Ala Cys Ile Gln Pro
            100                 105                 110

Gln Pro Thr Ala Gly Pro Arg Thr Arg Gly Arg Leu His His Trp Leu
        115                 120                 125

His Arg Leu Gln Glu Ala Pro Lys Lys Glu Ser Pro Gly Cys Leu Glu
    130                 135                 140

Ala Ser Val Thr Phe Asn Leu Phe Arg Leu Leu Thr Arg Asp Leu Lys
145                 150                 155                 160
```

```
Tyr Val Ala Asp Gly Asn Leu Cys Leu Arg Thr Ser Thr His Pro Glu
                165                 170                 175

Ser Thr

<210> SEQ ID NO 16
<211> LENGTH: 178
<212> TYPE: PRT
<213> ORGANISM: Artificial Sequence
<220> FEATURE:
<223> OTHER INFORMATION: FUSION POLYPEPTIDES

<400> SEQUENCE: 16

Met Lys Pro Thr Thr Thr Gly Lys Gly Cys His Ile Gly Gln Phe Lys
1               5                   10                  15

Ser Leu Ser Pro Gln Glu Leu Ala Ser Phe Lys Lys Ala Arg Asp Ala
                20                  25                  30

Leu Glu Glu Ser Leu Lys Leu Lys Asn Trp Ser Cys Ser Ser Pro Val
            35                  40                  45

Phe Pro Gly Asn Trp Asp Leu Arg Gln Leu Gln Val Arg Glu Arg Pro
        50                  55                  60

Val Ala Leu Glu Ala Glu Leu Ala Leu Thr Leu Lys Val Leu Glu Ala
65                  70                  75                  80

Thr Ala Asp Thr Asp Pro Ala Leu Gly Asp Val Leu Asp Gln Pro Leu
                85                  90                  95

His Thr Leu His His Ile Leu Ser Gln Leu Arg Ala Cys Ile Gln Pro
                100                 105                 110

Gln Pro Thr Ala Gly Pro Arg Thr Arg Gly Arg Leu His His Trp Leu
            115                 120                 125

His Arg Leu Gln Glu Ala Pro Lys Lys Glu Ser Ala Gly Cys Leu Glu
        130                 135                 140

Ala Ser Val Thr Phe Asn Leu Phe Arg Leu Leu Thr Arg Asp Leu Lys
145                 150                 155                 160

Tyr Val Ala Glu Gly Asn Leu Ser Leu Arg Thr Ser Thr His Pro Glu
                165                 170                 175

Ser Thr

<210> SEQ ID NO 17
<211> LENGTH: 169
<212> TYPE: PRT
<213> ORGANISM: Artificial Sequence
<220> FEATURE:
<223> OTHER INFORMATION: FUSION POLYPEPTIDES

<400> SEQUENCE: 17

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
                20                  25                  30

Leu Glu Glu Ser Leu Lys Leu Lys Asn Trp Ser Cys Ser Ser Pro Val
            35                  40                  45

Phe Pro Gly Asn Trp Asp Leu Arg Gln Leu Gln Val Arg Glu Arg Pro
        50                  55                  60

Val Ala Leu Glu Ala Glu Leu Ala Leu Thr Leu Lys Val Leu Glu Ala
65                  70                  75                  80

Thr Ala Asp Thr Asp Pro Ala Leu Gly Asp Val Leu Asp Gln Pro Leu
                85                  90                  95

His Thr Leu His His Ile Leu Ser Gln Leu Arg Ala Cys Ile Gln Pro
```

-continued

```
                100                 105                 110
Gln Pro Thr Ala Gly Pro Arg Thr Arg Gly Arg Leu His His Trp Leu
            115                 120                 125

His Arg Leu Gln Glu Ala Pro Lys Lys Glu Ser Pro Gly Cys Leu Glu
        130                 135                 140

Ala Ser Val Thr Phe Asn Leu Phe Arg Leu Leu Thr Arg Asp Leu Asn
145                 150                 155                 160

Ser Val Ala Ser Gly Asp Leu Ser Val
                165
```

<210> SEQ ID NO 18
<211> LENGTH: 174
<212> TYPE: PRT
<213> ORGANISM: Artificial Sequence
<220> FEATURE:
<223> OTHER INFORMATION: FUSION POLYPEPTIDES

<400> SEQUENCE: 18

```
Met Val Pro Val Ala Arg Leu Arg Gly Ala Leu Pro Asp Ala Arg Gly
1               5                   10                  15

Cys His Ile Ala Gln Phe Lys Ser Leu Ser Pro Gln Glu Leu Gln Ala
            20                  25                  30

Phe Lys Arg Ala Lys Asp Ala Leu Glu Glu Ser Leu Leu Leu Lys Asp
        35                  40                  45

Ser Lys Cys Arg Ser Arg Leu Phe Pro Arg Thr Trp Asp Leu Arg Gln
    50                  55                  60

Leu Gln Val Arg Glu Arg Pro Val Ala Leu Glu Ala Glu Leu Ala Leu
65                  70                  75                  80

Thr Leu Lys Val Leu Glu Ala Ala Gly Pro Ala Leu Glu Asp Val
                85                  90                  95

Leu Asp Gln Pro Leu His Thr Leu His His Ile Leu Ser Gln Leu Gln
            100                 105                 110

Ala Cys Ile Gln Pro Gln Pro Thr Ala Gly Pro Arg Pro Arg Gly Arg
        115                 120                 125

Leu His His Trp Leu His Arg Leu Gln Glu Ala Pro Lys Lys Glu Ser
    130                 135                 140

Pro Gly Cys Leu Glu Ala Ser Val Thr Phe Asn Leu Phe Arg Leu Leu
145                 150                 155                 160

Thr Arg Asp Leu Asn Ser Val Ala Ser Gly Asp Leu Ser Val
                165                 170
```

<210> SEQ ID NO 19
<211> LENGTH: 174
<212> TYPE: PRT
<213> ORGANISM: Artificial Sequence
<220> FEATURE:
<223> OTHER INFORMATION: FUSION POLYPEPTIDES

<400> SEQUENCE: 19

```
Met Val Pro Val Ala Arg Leu Arg Gly Ala Leu Pro Asp Ala Arg Gly
1               5                   10                  15

Cys His Ile Ala Gln Phe Lys Ser Leu Ser Pro Gln Glu Leu Gln Ala
            20                  25                  30

Phe Lys Arg Ala Lys Asp Ala Leu Glu Glu Ser Leu Leu Leu Lys Asp
        35                  40                  45

Ser Lys Cys Arg Ser Arg Leu Phe Pro Arg Thr Trp Asp Leu Arg Gln
    50                  55                  60
```

-continued

```
Leu Gln Val Arg Glu Arg Pro Val Ala Leu Glu Ala Glu Leu Ala Leu
65                  70                  75                  80

Thr Leu Lys Val Leu Glu Ala Ala Ala Gly Pro Ala Leu Glu Asp Val
                85                  90                  95

Leu Asp Gln Pro Leu His Thr Leu His His Ile Leu Ser Gln Leu Gln
                100                 105                 110

Ala Cys Ile Gln Pro Gln Pro Thr Ala Gly Pro Arg Pro Arg Gly Arg
            115                 120                 125

Leu His His Trp Leu His Arg Leu Gln Glu Ala Pro Lys Lys Glu Ser
        130                 135                 140

Ala Gly Cys Leu Glu Ala Ser Val Thr Phe Asn Leu Phe Arg Leu Leu
145                 150                 155                 160

Thr Arg Asp Leu Asn Ser Val Ala Ser Gly Asp Leu Ser Val
                165                 170
```

FUSION POLYPEPTIDES AND METHODS OF USE

CROSS REFERENCE

This application is a continuation application of U.S. patent application Ser. No. 15/107,101, filed Jun. 21, 2016, now U.S. Pat. No. 10,246,501, which is a national stage entry of International Patent Application No. PCT/CN2014/070328, filed Jan. 8, 2014, each of which is entirely incorporated herein by reference.

SEQUENCE LISTING

The instant application contains a Sequence Listing which has been filed electronically in ASCII format and is hereby incorporated by reference in its entirety. Said ASCII copy, created on Sep. 3, 2019, is named 45901-701_601_SL.txt and is 30,715 bytes in size.

BACKGROUND OF THE INVENTION

IL28B, together with IL28A and IL29, represents a subset (type—III) of the interferon family. Their expression can be induced by viral infections in a variety of human cell types (Nat Immunol. 2003; 4(1):69-77. Nat Immunol. 2003; 4(1): 63-68) and they can in turn bind and signal through a heterodimeric receptor complex composed of IL28R and IL10R2. The repertoire of genes induced by IL28B, IL28A and IL29 are essentially the same as that induced by interferon alpha. Amongst them are OAS1 and MX1, which bind and signal through a heterodimeric receptor complex composed of IFNAR1 and IFNAR2 (Gastroenterology. 2006; 131(6):1887-1898).

The antiviral activity induced by type-III interferon including IL28B, IL28A and IL29 has been demonstrated against encephalomyocarditis virus (EMCV), vesicular stomatitis virus (VSV), influenza (Eur J Immunol. 2004; 34(3):796-805. J Virol. 2006; 80(9):4501-4509.), hepatitis B virus (HBV) and hepatitis C virus (HCV) (J Virol. 2005; 79(6):3851-3854). However, the magnitude of antiviral response to type-III interferon is often smaller than that to interferon alpha in many cell types. A significant difference between type-III interferon and interferon alpha systems is the pattern of receptor distribution. While the receptors for interferon alpha are ubiquitously expressed, the IL28R component of the type-III interferon receptor is only present in a limited subset of cells, including hepatocytes (Cytokine 2005, 31, 109-118). Functional IL28R is notably absent from most hematopoietic cells (Hepatology. 2006; 44(4): 896-906). Preclinical toxicology studies have shown that a PEGylated IL29 peptide, unlike PEGylated interferon alpha, does not induce inhibition of bone marrow stem cell colony formation or induce antiviral and anti-proliferative activities in peripheral blood leukocytes (Ann NY Acad Sci. 2009; 1182:80-87).

About 150 million people worldwide are chronically infected with hepatitis C virus (HCV), which is the leading cause of cirrhosis, hepatocellular carcinoma, and liver transplantation (WHO. Hepatitis C fact sheet No. 164). HCV is considered a curable disease in the majority of patients. Current topline treatment regimens consist of PEGylated interferon alpha in combination with small molecule antivirals such as ribavirin (Health Technology Assessment 2004; Vol. 8: No. 39.), telaprevir and boceprevir (Ther Adv Gastroenterol 2012; 5(2) 139-151). Unfortunately, treatment with PEGylated interferon alpha is not always well tolerated, resulting in poor patient compliance. Major toxicities related to PEGylated interferon alpha include but are not limited to flu-like symptoms such as headache, fatigue and asthenia; neuropsychiatric abnormalities such as depression, anxiety and irritability; and more importantly, hematological disorders such as neutropenia and anemia. About 350 million people worldwide are chronically infected with hepatitis B virus (HBV). Current treatments include PEGylated interferon alpha and small molecule antivirals such as lamivudine, adefovir, tenofovir, telbivudine, and entecavir. Treatment of HBV with PEGylated interferon alpha results in similar toxicity as those of HCV.

SUMMARY OF THE INVENTION

As such, there exists a considerable need for new antiviral drugs for hepatitis C as well as for other diseases that are better tolerated and/or more effective than existing therapies. The present invention addresses this need and provides related advantages as well. The present invention encompasses modified human interleukin 28B (IL28B) and human interleukin 29 (IL29) fusion polypeptides. The invention also provides methods for the production of the fusion polypeptides, such as in prokaryotic systems like E. coli. Further, the invention discloses the pharmaceutical uses of the fusion polypeptides in the treatment of viral infections (including but not limited to hepatitis C, hepatitis B and influenza); autoimmune diseases (including but not limited to multiple sclerosis); and various type of cancers (including but not limited to hepatocellular carcinoma).

In one aspect, the invention provides a fusion polypeptide comprising a first fragment from a first interferon lambda isoform and a second fragment from a second interferon lambda isoform, wherein the first and second fragments are fused together at a fusion site to form a contiguous polypeptide, wherein the fusion site comprises a sequence of at least about 6 amino acids that is identical to a corresponding sequence in the first and the second interferon lambda isoforms.

In some cases, the fusion polypeptide can retains the secondary structure of the first or the second isoform. In some cases, the fusion polypeptide can be devoid of any additional T-epitope as compared to that of the first or the second isoform. In further cases, the fusion polypeptide can be devoid of any additional B-epitope as compared to that of the first or the second isoform In some examples, the first interferon lambda isoform can be an IL29 isoform. In some examples, the second interferon lambda isoform can be an IL28B isoform. In further examples, the first interferon lambda isoform can be an IL29 isoform and the second interferon lambda isoform can be an IL28B isoform.

In some examples, the fusion site can comprise a sequence of at least about 8 amino acids that is identical to a corresponding sequence in the first and the second interferon lambda isoforms.

In another aspect, the invention provides a fusion polypeptide having a structure of formula I:

(S1)-(helix A)-(S2)-(helix C)-(S3)-(helix D)-(S4)-(helix E)-(S5)-(helix F)-(S6)

wherein:
a. helix D comprises an amino acid sequence exhibiting at least 90% homology to a fragment having residues from about V98 to Q112 of IL28B (SEQ ID NO: 2) or from about V89 to Q103 of IL29 (SEQ ID NO: 1);

b. helix E comprises an amino acid sequence exhibiting at least 90% homology to a fragment having residues from about R130 to E145 of IL28B (SEQ ID NO:2) or from about R121 to E136 of IL29 (SEQ ID NO: 1);
c. each of S1, S2, S3, S4, S5 and S6 is independently a spacer sequence having between 1 to about 50 amino acid residues;

and wherein the fusion polypeptide is characterized in that:
i. helix A comprises an amino acid sequence exhibiting at least 95% homology to a fragment having residues from about P27 to L44 of IL28B (SEQ ID NO: 2), helix C comprises an amino acid sequence exhibiting at least 95% homology to a fragment having residues from about R56 to A80 of IL29 (SEQ ID NO: 1), and helix F comprises an amino acid sequence exhibiting at least 95% homology to a fragment having residues from about G139 to A161 of IL29 (SEQ ID NO: 1); or
ii. helix A comprises an amino acid sequence exhibiting at least 95% homology to a fragment having residues from about P20 to L37 of IL29 (SEQ ID NO: 1), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G148 to A170 of IL28B (SEQ ID NO: 2); or
iii. helix A comprises an amino acid sequence exhibiting at least 95% homology to a fragment having residues from about P27 to L44 of IL28B (SEQ ID NO: 2), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G139 to A161 of IL29 (SEQ ID NO: 1); or
iv. helix A comprises an amino acid sequence exhibiting at least 95% homology to a fragment having residues from about P20 to L37 of IL29 (SEQ ID NO: 1), helix C comprises an amino acid sequence exhibiting at least 95% homology to a fragment having residues from about R56 to A80 of IL29 (SEQ ID NO: 1), and helix F comprises an amino acid sequence exhibiting at least 95% homology to a fragment having residues from about G148 to A170 of IL28B (SEQ ID NO: 2); or
v. helix A comprises an amino acid sequence exhibiting at least 95% homology to a fragment having residues from about P27 to L44 of IL28B (SEQ ID NO: 2), helix C comprises an amino acid sequence exhibiting at least 95% homology to a fragment having residues from about R56 to A80 of IL29 (SEQ ID NO: 1), and helix F comprises an amino acid sequence exhibiting at least 95% homology to a fragment having residues from about G148 to A170 of IL28B (SEQ ID NO: 2); or
vi. helix A comprises an amino acid sequence exhibiting at least 95% homology to a fragment having residues from about P20 to L37 of IL29 (SEQ ID NO: 1), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G139 to A161 of IL29 (SEQ ID NO: 1).

In some cases, helix A can be identical to a fragment having residues from about P27 to L44 of IL28B (SEQ ID NO: 2). In other cases, helix A can be identical to a fragment having residues from about P20 to L37 of IL29 (SEQ ID NO: 1).

In some cases, helix C can be identical to a fragment having residues from about R63 to A87 of IL28B (SEQ ID NO: 2). In other cases, helix C can be identical to a fragment having residues from about R56 to A80 of IL29 (SEQ ID NO: 1).

In some cases, helix F can be identical to a fragment having residues from about G148 to A170 of IL28B (SEQ ID NO: 2). In other cases, helix F can be identical to a fragment having residues from about G139 to A161 of IL29 (SEQ ID NO: 1).

In some cases, S2 can further comprise a helix B.

In some cases, the fusion polypeptide can further comprise at least one modification in an amino acid residue corresponding to IL28B (SEQ ID NO: 2), wherein the at least one modification is selected from the group consisting of dV2, dP3, dV4, dA5, dR6, dL7, dR8, G9K, A10P, L11T, P12T, D13T, A14G, R15K, A20G, Q21R, Q31A, A32S, R35K, K37R, L45K, D48N, C49W, K50S, R52S, R54P, L55V, R58G, T59N, Q64L, T88A, dD90, dT91, D92P, G96E, R114Q, T127P, C168S, C175S, P3G, V4P, A5V, R6P, L7T and R8S.

In some cases, the fusion polypeptide can also comprise at least one modification in an amino acid residue corresponding to IL29 (SEQ ID NO: 1), wherein the at least one modification is selected from the group consisting of R14Q, L57Q, A81T, 82aD, 82bT, G83D, E87G, Q105R, P118T, and D162E.

In some cases, the fusion polypeptide can comprise a fusion site comprising a sequence of at least about 6 amino acids that is identical to a corresponding sequence in IL28B (SEQ ID NO: 2) and IL29 (SEQ ID NO: 1). In further cases, the fusion site can comprise a sequence of at least about 8 amino acids that is that is identical to a corresponding sequence in IL28B (SEQ ID NO: 2) and IL29 (SEQ ID NO: 1). In some examples, the fusion site can comprise a sequence of at least about 6-25 amino acids that is identical to a corresponding sequence of the at least two interferon lambda isoforms.

In some cases, the fusion polypeptide can retain the secondary structure of IL28B (SEQ ID NO: 2) or IL29 (SEQ ID NO: 1). In some cases, the fusion polypeptide can be devoid of any additional T-epitope as compared to that of IL28B (SEQ ID NO: 2) or IL29 (SEQ ID NO: 1). In some cases, the fusion polypeptide can be devoid of any additional B-epitope as compared to that of IL28B (SEQ ID NO: 2) or IL29 (SEQ ID NO: 1).

In some cases, the fusion polypeptide can exhibit at least 90% sequence homology to IL28B (SEQ ID NO: 2) or IL29 (SEQ ID NO: 1). In further cases, the fusion polypeptide can exhibit at least 95% sequence homology to IL28B (SEQ ID NO: 2) or IL29 (SEQ ID NO: 1).

In some cases, the N-terminus of the fusion polypeptide can be further modified by a polyethylene glycol (PEG). In some examples, the polyethylene glycol can be monomethoxy PEG propionaldehyde. In some examples, the polyethylene glycol can have a molecular weight of about 12 Kd to 40 Kd. In further cases, the PEGylated fusion polypeptide can exhibit a prolonged in vivo half-life as compared to IL28B (SEQ ID NO: 2) or IL29 (SEQ ID NO: 1).

In some cases, the fusion polypeptide can exhibit an enhanced chemistry stability as compared to IL28B (SEQ ID NO: 2) or IL29 (SEQ ID NO: 1).

In some examples, the fusion polypeptide can comprise an amino acid sequence selected from group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO: 13, SEQ ID NO:14, SEQ ID NO:15, SEQ ID NO:16, SEQ ID NO:17, SEQ ID NO:18, and SEQ ID NO: 19.

In yet another aspect, the invention provides a host cell expressing the fusion polypeptide. In some cases, the host cell can be a prokaryotic cell. In some examples, the prokaryotic cell can be *E. coli*. In other cases, the host cell can be a eukaryotic cell.

In one aspect, the invention provides a method of treating a viral infection in a mammal in need thereof, comprising administering to the mammal a therapeutically effective amount of the fusion polypeptide. In some cases, the viral infection can be inflicted by a virus selected from the group consisting of hepatitis B, hepatitis C, and influenza.

In another aspect, the invention provides a method of treating inflammation in a mammal in need thereof, comprising administering to the mammal a therapeutically effective amount of the fusion polypeptide. In some cases, the inflammation can be multiple sclerosis.

In yet another aspect, the invention provides a method of treating a cancer in a mammal in need thereof, comprising administering to the mammal a therapeutically effective amount of the fusion polypeptide. In some cases, the cancer can be selected from colon cancer, melanoma and hepatocellular carcinoma.

In one aspect, the invention provides a pharmaceutical composition comprising at least one of the fusion polypeptides and a pharmaceutically acceptable excipient.

In another aspect, the invention provides a pharmaceutical composition comprising at least one of the fusion polypeptides and a second therapeutic agent.

In yet another aspect, the invention provides a vector comprising a polynucleotide encoding the fusion polypeptide.

In a further aspect, the invention provides a method of producing the fusion polypeptide, comprising expressing the vector in a cell under conditions suitable for protein expression, thereby producing the fusion polypeptide.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 16 illustrates the various treatment conditions of the H3N2-infected A549 cells in the 96 well plates.

DETAILED DESCRIPTION OF THE INVENTION

Figure 1:
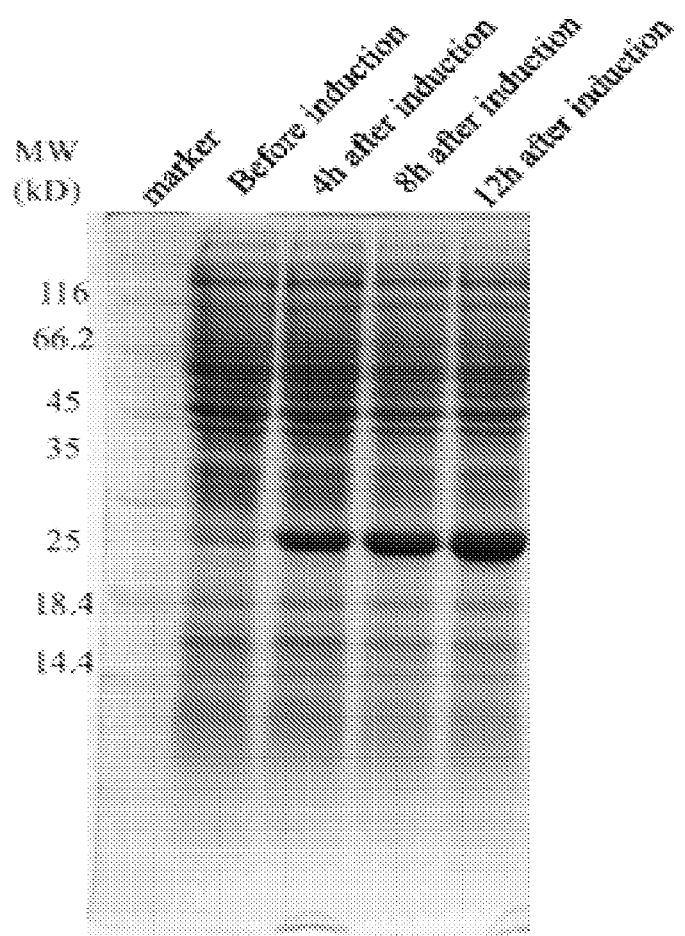
FIG. 1 illustrates the SDS-PAGE analysis following the protein expression of a fusion polypeptide (SEQ ID NO: 8) using the methods of the present invention.

Before the embodiments of the invention are described, it is to be understood that such embodiments are provided by way of example only, and that various alternatives to the embodiments of the invention described herein may be employed in practicing the invention Numerous variations, changes, and substitutions will now occur to those skilled in the art without departing from the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

As used in the specification and claims, the singular forms "a", "an" and "the" include plural references unless the context clearly dictates otherwise.

The terms "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component.

The term "amino acid" refers to either natural and/or unnatural or synthetic amino acids, including but not limited to both the D or L optical isomers, and amino acid analogs and peptidomimetics. Standard single or three letter codes are used to designate amino acids.

The term "natural L-amino acid" means the L optical isomer forms of glycine (G), proline (P), alanine (A), valine (V), leucine (L), isoleucine (I), methionine (M), cysteine (C), phenylalanine (F), tyrosine (Y), tryptophan (W), histidine (H), lysine (K), arginine (R), glutamine (Q), asparagine (N), glutamic acid (E), aspartic acid (D), serine (S), and threonine (T).

The term "non-naturally occurring," as applied to sequences and as used herein, means polypeptide or polynucleotide sequences that do not have a counterpart to, are not complementary to, or do not have a high degree of homology with a wild-type or naturally-occurring sequence found in a mammal. For example, a non-naturally occurring polypeptide or fragment may share no more than 99%, 98%, 95%, 90%, 80%, 70%, 60%, 50% or even less amino acid sequence identity as compared to a natural sequence when suitably aligned.

The terms "hydrophilic" and "hydrophobic" refer to the degree of affinity that a substance has with water. A hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be characterized based on their hydrophobicity. A number of scales have been developed. An example is a scale developed by Levitt, M, et al., J Mol Biol (1976) 104:59, which is listed in Hopp, T P, et al., Proc Natl Acad Sci USA (1981) 78:3824. Examples of "hydrophilic amino acids" are arginine, lysine, threonine, alanine, asparagine, and glutamine. Of particular interest are the hydrophilic amino acids aspartate, glutamate, and serine, and glycine. Examples of "hydrophobic amino acids" are tryptophan, tyrosine, phenylalanine, methionine, leucine, isoleucine, and valine.

A "fragment" when applied to a protein, is a truncated form of a native biologically active protein that may or may not retain at least a portion of the therapeutic and/or biological activity. A "variant" when applied to a protein is a protein with sequence homology to the native biologically active protein that retains at least a portion of the therapeutic and/or biological activity of the biologically active protein. For example, a variant protein may share at least 70%, 75%, 80%, 85%, 90%, 95%, 96%, 97%, 98% or 99% amino acid sequence identity compared with the reference biologically active protein. As used herein, the term "biologically active protein moiety" includes proteins modified deliberately, as for example, by site directed mutagenesis, synthesis of the encoding gene, insertions, or accidentally through mutations.

"Conjugated", "linked," "fused," and "fusion" are used interchangeably herein. These terms refer to the joining together of two or more chemical elements, sequences or components, by whatever means including chemical conjugation or recombinant means. For example, a promoter or enhancer is operably linked to a coding sequence if it affects the transcription of the sequence. Generally, "operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. Thus, the resulting "fusion polypeptide" is a single protein containing two or more fragments that correspond to polypeptides encoded by the original ORFs (which segments are not normally so joined in nature). The "fusion site" refers to the sequence where the two or more fragments are joined together. In some cases, the fusion site can be a sequence that is identical in the two or more fragments. For example, the fusion site can be a sequence of about 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids that is identical in the joined fragments. In specific examples, the fusion site can be a sequence of about 6, 7, 8, 9, 10, 11, 12, 13, 14, 15, 16, 17, 18, 19, 20, 21, 22, 23 or 24 amino acids that is identical in the joined fragments.

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide that is known to comprise additional residues in one or both directions.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "gene" and "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

"Homology" or "homologous" or "sequence identity" refers to sequence similarity or interchangeability between two or more polynucleotide sequences or between two or more polypeptide sequences. When using a program such as Emboss Needle or BestFit to determine sequence identity, similarity or homology between two different amino acid sequences, the default settings may be used, or an appropriate scoring matrix, such as blosum45 or blosum80, may be selected to optimize identity, similarity or homology scores. Preferably, polynucleotides that are homologous are those which hybridize under stringent conditions as defined herein and have at least 70%, preferably at least 80%, more preferably at least 90%, more preferably 95%, more preferably 97%, more preferably 98%, and even more preferably 99% sequence identity compared to those sequences. Polypeptides that are homologous preferably have sequence identities of at least 80%, or at least 90%, or at least 95%, or at least 97%, or at least 98%, or have at least 99% sequence identity when sequences of comparable length are optimally aligned.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined polynucleotide sequence, or may be measured over a shorter length, for example, over the length of a fragment taken from a larger, defined polynucleotide sequence, for instance, a fragment of at least 45, at least 60, at least 90, at least 120, at least 150, at least 210 or at least 450 contiguous residues. Such lengths are exemplary only, and it is understood that any fragment length supported by the sequences shown herein, in the tables, figures or Sequence Listing, may be used to describe a length over which percentage identity may be measured.

"Percent (%) sequence identity," with respect to the polypeptide sequences identified herein, is defined as the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide sequence, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vitro with a vector of this invention. In some cases, a host cell is a prokaryotic cell. In some examples, the prokaryotic cell is E. coli. In other cases, a host cell is a eukaryotic cell.

A "vector" is a nucleic acid molecule, preferably self-replicating in an appropriate host, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. target gene induction and/or apoptosis. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal so that both agents and/or their metabolites are present in the subject at the same time. Co-administration includes simultaneous administration in separate compositions, administration at different times in separate compositions, or administration in a composition in which both agents are present.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like, when the molecule contains an acidic functionality; and when the molecule contains a basic functionality, salts of organic or inorganic acids, such as hydrochloride, hydrobromide, tartrate, mesylate (methane sulfonate), ethane sulfonate, acetate, maleate, oxalate, phosphate, and the like. In a compound with more than one basic moiety, more than one of the basic moieties may be converted to the salt form, including but not limited to a bis- or tris-salt. Alternatively, a compound having more than one basic moiety may form a salt at only one of the basic moieties.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting or enhancing the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

The term "in vivo" refers to an event that takes place in a subject's body.

The term "in vitro" refers to an event that takes places outside of a subject's body. For example, an in vitro assay encompasses any assay run outside of a subject assay. in vitro assays encompass cell-based assays in which cells alive or dead are employed. in vitro assays also encompass a cell-free assay in which no intact cells are employed.

Nomenclature of Polypeptides

Polypeptides are named herein using, interchangeably, polypeptide nomenclature, organic chemical nomenclature, chemical formula, amino acid sequences, or a mix thereof. For example, a substitution in an analogue of IL28B maybe indicated as "Original amino acid-position-substituted amino acid".

Accordingly, the notation "C175S IL28B" or "Cys175Ser IL28B" means that the IL28B analogue comprises a substitution of cysteine with serine at the analogue amino acid position corresponding to the amino acid at position 175 in IL28B (SEQ ID NO: 2) when the analogue and IL28B are aligned as described below ("alignment"). Multiple substitutions may be separated by commas (with a space after the comma) and surrounded by brackets in order to make it clear that they belong to the same analogue. Accordingly, "(C168S, C175S) IL28B" means that the IL28B analogue comprises two substitutions of cysteine's with serine's at the analogue amino acid positions corresponding to the amino acid at positions 168 and 175 in IL28B (SEQ ID NO:2).

An extension in an analogue of IL28B may be described by reference to SEQ ID NO: 2 by addition of position numbers (continued positive numbers in the C-terminus and negative numbers in the N-terminus) or, more simply, by adding the amino acids of the extension in question, using the correct sequence thereof, to the compound in question. Accordingly, M-IL28B designates the polypeptide of SEQ ID NO: 2 with an M at position −1 by reference to SEQ ID NO: 2.

An insertion in an analogue of IL29 may be described as: "Amino acid position number before the insertion-index-inserted amino acid". The amino acid position number before the insertion refers to the amino acid position in IL29 (SEQ ID NO: 1) just before the gap, which is created when the insertion analogue and IL29 are aligned as described below ("alignment"). The index is a lower case letter in alphabetical order, e.g. "a" for the first inserted amino acid, "b" for the second inserted amino acid, etc. Accordingly, "82aD IL29" designates an analogue of IL29 with an insertion of glycine after amino acid position 82 in IL29 (SEQ ID NO: 1).

A deletion in an analogue of IL28B may be described as: "des Deleted amino acid-deleted amino acid position" or "d Deleted amino acid-deleted amino acid position". The deleted amino acid position refers to the amino acid position in IL28B (SEQ ID NO: 2) at the gap, which is created when the analogue and IL28B are aligned as described below ("alignment"). Accordingly, "des V2 IL28B" designates an analogue of IL28B with a deletion of the valine residue at position 2 in IL28B (SEQ ID NO: 2).

Where desired, the alignment of two amino acid sequences may be made by using the Needle program from the EMBOSS package (www.ebi.ac.uk). The Needle program implements a global alignment algorithm (J. Mol. Biol. 1970, 48:443-453). The substitution matrix used is BLOSUM62, gap opening penalty is 50, and gap extension penalty is 0.5.

Fusion Polypeptides, Host Cells and Vectors

The present invention relates to fusion polypeptides that are useful for the treatment of disease conditions in mammals. The fusion polypeptide can comprise a first fragment from a first isoform and a second fragment from a second isoform of a protein family. In some cases, the first and second isoforms can both be members of a same protein family. In other cases, the first and second isoforms can belong to different protein families. In some examples, the fusion polypeptides can comprise fragments from a first and a second interferon lambda isoform. Examples of interferon lambda isoforms include but are not limited various isoforms of IL28A, IL28B and IL29. In some examples, the first interferon lambda isoform is an IL28B isoform including but not limited to those described in SEQ ID NO: 2. In some examples, the second interferon lambda isoform is an IL29 isoform including but not limited to those described in SEQ ID NO: 1. In further examples, the first interferon lambda isoform is an IL28B isoform and the second interferon lambda isoform is an IL29 isoform.

In some cases, the fragments can be fused together at a fusion site and thereby form a contiguous polypeptide. In some examples, the fusion site can comprise a sequence of at least about 6 amino acids that is identical to a corresponding sequence that is found in the first and the second isoform. In further examples, the fusion site can comprise a sequence of at least about 7, 8, 9, 10, 11, 12, 13, 14, 15, 16, 17, 18, 19, 20, 21, 22, 23, 24, 25, 26, 27, 28, 29 or 30 amino acids that is identical to a corresponding sequence that is found in the first and the second isoforms. In the cases wherein the first and second isoform are each interferon lambda isoforms, the fusion site can comprise a sequence of at least about 7, 8, 9, 10, 11, 12, 13, 14, 15, 16, 17, 18, 19, 20, 21, 22, 23, 24, 25, 26, 27, 28, 29 or 30 amino acids that is identical to a corresponding sequence that is found in the first and the second interferon lambda isoforms.

Not wishing to be bound by any particular theory, having a fusion site sharing sequence identity to the first and the second isoforms is particularly advantageous for avoiding new epitopes, and hence undesired immunogenicity resulting from the fusion event. In general, T cells are rigorously selected for survival, and they undergo both positive and negative selection to produce T cells that recognize self-major histocompatibility complex (MHC) molecules but do not recognize native peptides. T cell epitopes presented by MHC class I molecules are typically peptides between 8 and 11 amino acids in length, whereas MHC class II molecules present longer peptides, 13-17 amino acids in length. A fusion polypeptide, while non-native as a whole, can therefore be rendered non-immunogenic or poorly so if all possible peptide sequences representing the T cell epitopes are native. By selecting a fusion site in the middle of an amino acid fragment with at least 6 consecutive amino acids that are identical in both fusion partners (to avoid the predominant non-native MHC class I binding 9mer T epitopes), at least 10 consecutive amino acids that are identical in both fusion partners (to avoid most non-native MHC class I binding T epitopes), or at least 16 consecutive amino acids that are identical in both fusion partners (to avoid most non-native MHC class II in addition to MHC class I binding T epitopes), fusion polypeptides with minimal immunogenicity may be generated in a predictable manner.

In some cases, the fusion polypeptide can have a structure of Formula I:

(S1)-(helix A)-(S2)-(helix C)-(S3)-(helix D)-(S4)-(helix E)-(S5)-(helix F)-(S6)

wherein each of helix A, helix C, helix D, helix E and helix F is independently an alpha helix, and wherein each of S1, S2, S3, S4, S5 and S6 is independently a spacer sequence.

In some cases, helix A can comprise an amino acid sequence exhibiting at least about 50%, 60%, 70%, 80%, 90%, 95%, 99% or 100% homology to a fragment having residues from about P27 to L44 of IL28B peptide (SEQ ID NO:2) or from about P20 to L37 of IL29 peptide (SEQ ID NO:1). In some examples, helix A can be identical to a fragment having residues from about P27 to L44 of IL28B peptide (SEQ ID NO: 2). In other examples, helix A can be identical to a fragment having residues from about P20 to L37 of IL29 peptide (SEQ ID NO: 1).

In some cases, helix C can comprise an amino acid sequence exhibiting at least about 50%, 60%, 70%, 80%, 90%, 95%, 99% or 100% homology to a fragment having residues from about R63 to A87 of IL28B peptide (SEQ ID NO:2) or from about R56 to A80 of IL29 peptide (SEQ ID NO:1). In some examples, helix C can be identical to a fragment having residues from about R63 to A87 of IL28B peptide (SEQ ID NO: 2). In other examples, helix C can be identical to a fragment having residues from about R56 to A80 of IL29 peptide (SEQ ID NO: 1).

In some cases, helix D can comprise an amino acid sequence exhibiting at least about 50%, 60%, 70%, 80%, 90%, 95%, 99% or 100% homology to a fragment having residues from about V98 to Q112 of IL28B peptide (SEQ ID NO:2) or from about V89 to Q103 of IL29 peptide (SEQ ID NO: 1). In some examples, helix D can be identical to a fragment having residues from about V98 to Q112 of IL28B peptide (SEQ ID NO:2). In other examples, helix D can be identical to a fragment having residues from about V89 to Q103 of IL29 peptide (SEQ ID NO: 1).

In some cases, helix E can comprise an amino acid sequence exhibiting at least about 50%, 60%, 70%, 80%, 90%, 95%, 99% or 100% homology to a fragment having residues from about R130 to E145 of IL28B peptide (SEQ ID NO:2) or from about R121 to E136 of IL29 peptide (SEQ ID NO: 1). In some examples, helix E can be identical to a fragment having residues from about R130 to E145 of IL28B peptide (SEQ ID NO:2). In other examples, helix E can be identical to a fragment having residues from about R121 to E136 of IL29 peptide (SEQ ID NO: 1).

In some cases, helix F can comprise an amino acid sequence exhibiting at least about 50%, 60%, 70%, 80%, 90%, 95%, 99% or 100% homology to a fragment having residues from about G148 to A170 of IL28B (SEQ ID NO: 2) or from about G139 to A161 of IL29 (SEQ ID NO: 1). In some examples, helix F can be identical to a fragment having residues from about G148 to A170 of IL28B (SEQ ID NO: 2). In other examples, helix F can be identical to a fragment having residues from about G139 to A161 of IL29 (SEQ ID NO: 1).

In some cases, each of S1, S2, S3, S4, S5 and S6 can independently have between 1 to about 5, between 1 to about 10, between 1 to about 15, between 1 to about 20, between 1 to about 30, between 1 to about 40, between 1 to about 50, between 1 to about 60, between 1 to about 80, or between 1 to about 100 amino acid residues. In some examples, S2 can further comprise a helix B.

In some embodiments, helix A can comprise an amino acid sequence exhibiting at least about 80%, 90%, 95%, 99% or 100% homology to a fragment having residues from about P27 to L44 of IL28B (SEQ ID NO: 2), helix C can comprise an amino acid sequence exhibiting at least about 80%, 90%, 95%, 99% or 100% homology to a fragment having residues from about R56 to A80 of IL29 (SEQ ID NO: 1), and helix F can comprise an amino acid sequence exhibiting at least about 80%, 90%, 95%, 99% or 100% homology to a fragment having residues from about G139 to A161 of IL29 (SEQ ID NO: 1). For example, helix A can comprise an amino acid sequence exhibiting at least 95% homology to a fragment having residues from about P27 to L44 of IL28B (SEQ ID NO: 2), helix C can comprise an amino acid sequence exhibiting at least 95% homology to a fragment having residues from about R56 to A80 of IL29 (SEQ ID NO: 1), and helix F can comprise an amino acid sequence exhibiting at least 95% homology to a fragment having residues from about G139 to A161 of IL29 (SEQ ID NO: 1).

In other embodiments, helix A can comprise an amino acid sequence exhibiting at least about 50%, 60%, 70%, 80%, 90%, 95%, 99% or 100% homology to a fragment having residues from about P20 to L37 of IL29 (SEQ ID NO: 1), helix C can comprise an amino acid sequence exhibiting at least about 50%, 60%, 70%, 80%, 90%, 95%, 99% or 100% homology to a fragment having residues from about R63 to A87 of IL28B (SEQ ID NO: 2), and helix F can comprise an amino acid sequence exhibiting at least about 50%, 60%, 70%, 80%, 90%, 95%, 99% or 100% homology to a fragment having residues from about G148 to A170 of IL28B (SEQ ID NO: 2). For example, helix A can comprise an amino acid sequence exhibiting at least 95% homology to a fragment having residues from about P20 to L37 of IL29 (SEQ ID NO: 1), helix C can comprise an amino acid sequence exhibiting at least 95% homology to a fragment having residues from about R63 to A87 of IL28B (SEQ ID NO: 2), and helix F can comprise an amino acid sequence exhibiting at least 95% homology to a fragment having residues from about G148 to A170 of IL28B (SEQ ID NO: 2).

In yet other embodiments, helix A can comprise an amino acid sequence exhibiting at least about 50%, 60%, 70%, 80%, 90%, 95%, 99% or 100% homology to a fragment having residues from about P27 to L44 of IL28B (SEQ ID NO: 2), helix C can comprise an amino acid sequence exhibiting at least about 50%, 60%, 70%, 80%, 90%, 95%, 99% or 100% homology to a fragment having residues from about R63 to A87 of IL28B (SEQ ID NO: 2), and helix F can comprise an amino acid sequence exhibiting at least about 50%, 60%, 70%, 80%, 90%, 95%, 99% or 100% homology to a fragment having residues from about G139 to A161 of IL29 (SEQ ID NO: 1). For example, helix A can comprise an amino acid sequence exhibiting at least 95% homology to a fragment having residues from about P27 to L44 of IL28B (SEQ ID NO: 2), helix C can comprise an amino acid sequence exhibiting at least 95% homology to a fragment having residues from about R63 to A87 of IL28B (SEQ ID NO: 2), and helix F can comprise an amino acid sequence exhibiting at least 95% homology to a fragment having residues from about G139 to A161 of IL29 (SEQ ID NO: 1).

In some embodiments, helix A can comprise an amino acid sequence exhibiting at least about 50%, 60%, 70%, 80%, 90%, 95%, 99% or 100% homology to a fragment having residues from about P20 to L37 of IL29 (SEQ ID NO: 1), helix C can comprise an amino acid sequence exhibiting at least about 50%, 60%, 70%, 80%, 90%, 95%, 99% or 100% homology to a fragment having residues from about R56 to A80 of IL29 (SEQ ID NO: 1), and helix F can comprise an amino acid sequence exhibiting at least about 50%, 60%, 70%, 80%, 90%, 95%, 99% or 100% homology to a fragment having residues from about G148 to A170 of IL28B (SEQ ID NO: 2). For example, helix A can comprise an amino acid sequence exhibiting at least 95% homology to a fragment having residues from about P20 to L37 of IL29 (SEQ ID NO: 1), helix C can comprise an amino acid sequence exhibiting at least 95% homology to a fragment having residues from about R56 to A80 of IL29 (SEQ ID NO: 1), and helix F can comprise an amino acid sequence exhibiting at least 95% homology to a fragment having residues from about G148 to A170 of IL28B (SEQ ID NO: 2).

In other embodiments, helix A can comprise an amino acid sequence exhibiting at least about 50%, 60%, 70%, 80%, 90%, 95%, 99% or 100% homology to a fragment having residues from about P27 to L44 of IL28B (SEQ ID NO: 2), helix C can comprise an amino acid sequence exhibiting at least about 50%, 60%, 70%, 80%, 90%, 95%, 99% or 100% homology to a fragment having residues from about R56 to A80 of IL29 (SEQ ID NO: 1), and helix F can comprise an amino acid sequence exhibiting at least about 50%, 60%, 70%, 80%, 90%, 95%, 99% or 100% homology to a fragment having residues from about G148 to A170 of IL28B (SEQ ID NO: 2). For example, helix A can comprise an amino acid sequence exhibiting at least 95% homology to a fragment having residues from about P27 to L44 of IL28B (SEQ ID NO: 2), helix C can comprise an amino acid sequence exhibiting at least 95% homology to a fragment having residues from about R56 to A80 of IL29 (SEQ ID NO: 1), and helix F can comprise an amino acid sequence exhibiting at least 95% homology to a fragment having residues from about G148 to A170 of IL28B (SEQ ID NO: 2).

In yet other embodiments, helix A can comprise an amino acid sequence exhibiting at least about 50%, 60%, 70%, 80%, 90%, 95%, 99% or 100% homology to a fragment having residues from about P20 to L37 of IL29 (SEQ ID NO: 1), helix C can comprise an amino acid sequence exhibiting at least about 50%, 60%, 70%, 80%, 90%, 95%, 99% or 100% homology to a fragment having residues from about R63 to A87 of IL28B (SEQ ID NO: 2), and helix F can comprise an amino acid sequence exhibiting at least about 50%, 60%, 70%, 80%, 90%, 95%, 99% or 100% homology to a fragment having residues from about G139 to A161 of IL29 (SEQ ID NO: 1). For example, helix A can comprise an amino acid sequence exhibiting at least 95% homology to a fragment having residues from about P20 to L37 of IL29 (SEQ ID NO: 1), helix C can comprise an amino acid sequence exhibiting at least 95% homology to a fragment having residues from about R63 to A87 of IL28B (SEQ ID NO: 2), and helix F can comprise an amino acid sequence exhibiting at least 95% homology to a fragment having residues from about G139 to A161 of IL29 (SEQ ID NO: 1).

In some cases, the fusion polypeptides can retain the secondary structure of the first and/or the second isoform. The secondary structure of an isoform can be defined by the number and/or order of secondary units including but not limited to alpha-helices and beta-sheets. In some examples, the fusion polypeptide can comprise the same number and order of secondary units as those of the first and/or the second isoform. In the cases wherein the first and second isoform are each interferon lambda isoforms, the fusion polypeptide can retain the secondary structure of IL28B peptide (SEQ ID NO: 2) or IL29 peptide (SEQ ID NO: 1).

In some cases, the fusion polypeptides can be substantially free of epitopes recognized by human T cells. The elimination of such epitopes for the purpose of generating less immunogenic proteins has been disclosed previously; see for example WO 98/52976, WO 02/079232, and WO 00/3317 which are incorporated by reference herein. Assays for human T cell epitopes have been described (Stickler, M., et al. (2003) $J$ $Immunol$ $Methods$, 281: 95-108). Of particular interest are peptide sequences that can be oligomerized without generating T-cell epitopes or non-human sequences. This is achieved by testing direct repeats of these sequences for the presence of T-cell epitopes and for the occurrence of 6 to 15-mer and, in particular, 9-mer sequences that are not human, and then altering the design of the XTEN sequence to eliminate or disrupt the epitope sequence. With a reduction in the numbers of epitopes capable of binding to MHC receptors, there is a concomitant reduction in the potential for T cell activation as well as T cell helper function, reduced B cell activation or upregulation and reduced antibody production. The low degree of predicted T-cell epitopes can be determined by epitope prediction algorithms such as, e.g., TEPITOPE (Sturniolo, T., et al. (1999) Nat Biotechnol, 17: 555-61).

In some cases, the fusion polypeptide can be devoid of any additional T-epitope as compared to that of IL28B peptide (SEQ ID NO: 2) or IL29 peptide (SEQ ID NO: 1). In further cases, the fusion polypeptide can have less T-epitopes as compared to that of IL28B peptide (SEQ ID NO: 2) or IL29 peptide (SEQ ID NO: 1).

In some cases, the fusion polypeptide can be devoid of any additional B-epitope as compared to that of IL28B peptide (SEQ ID NO: 2) or IL29 peptide (SEQ ID NO: 1). In further cases, the fusion polypeptide can have less B-epitopes as compared to that of IL28B peptide (SEQ ID NO: 2) or IL29 peptide (SEQ ID NO: 1).

In various cases, the fusion polypeptides can further comprise at least one modification in an amino acid residue corresponding to IL28B peptide (SEQ ID NO: 2), wherein the at least one modification is selected from the group consisting of dV2, dP3, dV4, dA5, dR6, dL7, dR8, G9K, A10P, L11T, P12T, D13T, A14G, R15K, A20G, Q21R, Q31A, A32S, R35K, K37R, L45K, D48N, C49W, K50S, R52S, R54P, L55V, R58G, T59N, Q64L, T88A, dD90, dT91, D92P, G96E, R114Q, T127P, C168S, C175S, P3G, V4P, A5V, R6P, L7T and R8S.

In various cases, the fusion polypeptides can further comprise at least one modification in an amino acid residue corresponding to IL29 peptide (SEQ ID NO: 1), wherein the at least one modification is selected from the group consisting of R14Q, L57Q, A81T, 82aD, 82bT, G83D, E87G, Q105R, P118T, and D162E.

In some cases, the fusion polypeptides can further comprise a fusion site comprising a sequence of at least about 2, 3, 4, 5, 6, 7, 8, 9 or 10 amino acids that is identical to a corresponding sequence in IL28B (SEQ ID NO: 2) and IL29 (SEQ ID NO: 1). In other cases, the fusion site can comprise a sequence of about 11, 12, 13, 14, 15, 16, 17, 18, 19, 20, 21, 22, 23, 24, 25, 26, 27, 28, 29 or 30 amino acids that is identical to a corresponding sequence in IL28B (SEQ ID NO:2) and IL29 (SEQ ID NO: 1).

In some cases, the fusion site can comprises a sequence of at least about 2 to 30, about 3 to 25, about 4 to 20, about 5 to 15, or about 6 to 10 amino acids that is identical to a corresponding sequence of the at least two interferon lambda isoforms.

In some cases, the fusion polypeptide can exhibit at least about 80%, 81%, 82%, 83%, 84%, 85%, 86%, 87%, 88%, 89%, 90%, 91%, 92%, 93%, 94%, 95%, 96%, 97%, 98%, or 99% sequence homology to IL28B (SEQ ID NO: 2). For example, the fusion polypeptide can exhibit at least about 90% sequence homology to IL28B (SEQ ID NO: 2). Further, the fusion polypeptide can exhibit at least about 95% sequence homology to IL28B (SEQ ID NO: 2).

In some cases, the fusion polypeptide can exhibit less than about 10%, 20%, 30%, 40%, 50%, 60%, 70%, 80%, 90%, 95% or 99% sequence homology to IL28B (SEQ ID NO: 2). For example, the fusion polypeptide can exhibit less than about 80% sequence homology to IL28B (SEQ ID NO: 2). Further, the fusion polypeptide can exhibit less than about 50% sequence homology to IL28B (SEQ ID NO: 2).

In some cases, the fusion polypeptide can exhibit at least about 80%, 81%, 82%, 83%, 84%, 85%, 86%, 87%, 88%, 89%, 90%, 91%, 92%, 93%, 94%, 95%, 96%, 97%, 98%, or 99% sequence homology to IL29 (SEQ ID NO: 1). For example, the fusion polypeptide can exhibit at least about 90% sequence homology to IL29 (SEQ ID NO: 1). Further, the fusion polypeptide can exhibit at least about 95% sequence homology to IL29 (SEQ ID NO: 1).

In some cases, the fusion polypeptide can exhibit less than about 10%, 20%, 30%, 40%, 50%, 60%, 70%, 80%, 90%, 95% or 99% sequence homology to IL29 (SEQ ID NO: 1). For example, the fusion polypeptide can exhibit less than about 90% sequence homology to IL29 (SEQ ID NO: 1). Further, the fusion polypeptide can exhibit less than about 50% sequence homology to IL29 (SEQ ID NO: 1).

In some cases, the fusion polypeptide can be further modified. The modification can occur at either the N-terminus, C-terminus, or at any reactive amino acid side chain.

In some embodiments, the fusion polypeptide can be further modified by a polyethylene glycol (PEG). Examples of polyethylene glycol include but are not limited to monomethoxy PEG maleimide, monomethoxy PEG iodoacetamide or monomethoxy PEG propionaldehyde. Further, the polyethylene glycol can have a molecular weight of about 1 Kd to 200 Kd, about 5 Kd to 200 Kd, about 5 Kd to 150 Kd, about 8 Kd to 150 Kd, about 8 Kd to 100 Kd, about 10 Kd to 100 Kd, about 10 Kd to 50 Kd, about 12 Kd to 50 Kd, or about 12 Kd to 40 Kd.

In some cases, the PEGylated fusion polypeptide can exhibit a prolonger in vitro half-life as compared to the first and the second member of the protein family. For example, the fusion polypeptide can exhibits a prolonged in vitro half-life as compared to IL28B (SEQ ID NO:2) or IL29 (SEQ ID NO:1).

In some cases, the fusion polypeptide can exhibit an enhanced chemistry stability as compared to the first and the second member of the protein family. For example, the fusion polypeptide can exhibit an enhanced chemistry stability as compared to IL28B (SEQ ID NO: 2) or IL29 (SEQ ID NO: 1).

The fusion polypeptide can comprise an amino acid sequence selected from group consisting of SEQ ID NO:3, SEQ ID NO:4, SEQ ID NO:5, SEQ ID NO: 6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

The present invention also provides host cells expressing the fusion proteins disclosed herein. A host cell includes an individual cell, cell culture, or cell line. Host cells include progeny of a single host cell. A host cell can be transfected with a heterologous sequence including vectors of the present disclosure. Host cells may be prokaryotic or eukaryotic, such as bacterial cells, fungal cells, animal cells, insect cells, plant cells and the like. Examples of bacterial host cells include microorganisms belonging to the genus *Escherichia, Serratia, Bacillus, Brevibacterium, Corynebacterium, Microbacterium, Pseudomonas* and the like. For example, bacterial host cells may include, but not be limited to, *Escherichia coli* XL1-Blue, XL2-Blue, DH1, MC1000, KY3276, W1485, JM109, HB101, No. 49, i W3110, NY49, G1698, BL21, or TB1. Other bacterial host cells may include, but not be limited to, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 13869, *Corynebacterium acetoacidophilum* ATCC 13870, *Microbacterium ammoniaphilum* ATCC 15354, *Pseudomonas putida, Pseudomonas* sp. D-0110 and the like.

Yeast host cells may include microorganisms belonging to the genus *Kluyveromyces, Trichosporon, Saccharomyces, Schizosaccharomyces, Schwanniomyces, Pichia, Candida* and the like, such as *Saccharomyces cerevisiae, Schizosaccharomyces pombe, Kluyveromyces lactis, Trichosporon pullulans, Schwanniomyces alluvius, Candida utilis* and the like.

Examples of eukaryotic cells include animal cells such as mammalian cells. For example, host cells include, but are not limited to, Chinese hamster ovary cells (CHO) or monkey cells, such as COS cells, HepG2 cells, A549 cells, and any cells that are available through ATCC or other depositories.

The host cells of the present disclosure may be grown in cultures, and in any apparatus that may be used to grow cultures, including fermentors. They may be grown as monolayers or attached to a surface. Alternatively, the host cells may be grown in suspension. The cells can be grown in a culture medium that is serum-free. The media can be a commercially available media, such as, but not limited to, OPTI-CHO medium (Invitrogen, Catalogue #12681) supplemented with glutamine, such as 8 mM L-glutamine.

The host cells of the present disclosure may comprise a heterologous sequence to effect expression of the subject fusion polypeptides. The heterologous sequence may comprise a vector, which is a nucleic acid molecule, preferably self-replicating, which transfers an inserted nucleic acid molecule into and/or between host cells. Vectors may include those that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An expression vector is a polynucleotide which, when introduced into an appropriate host cell, can be transcribed and translated into a polypeptide(s).

The heterologous sequence encoding a fusion protein of the present invention can be expressed by a single or multiple vectors. The nucleic acid sequences can be arranged in any order in a single operon, or in separate operons that are placed in one or multiple vectors. Where desired, two or more expression vectors can be employed, each of which contains one or more heterologous sequences operably linked in a single operon. Linked refers to the joining together of two more chemical elements or components, by whatever means including chemical conjugation or recombinant means. Operably-linked refers to a juxtaposition wherein the components so described are in a relationship permitting them to function in their intended manner. For instance, a promoter sequence is linked, or operably linked, to a coding sequence if the promoter sequence promotes transcription of the coding sequence. The subject vectors can stay replicable episomally, or as an integral part of the host cell genome.

The heterologous sequences of the present disclosure can be under the control of a single regulatory element. In some cases, the heterologous nucleic acid sequences are regulated by a single promoter. In other cases, the heterologous nucleic acid sequences are placed within a single operon. In still other cases, the heterologous nucleic acid sequences are placed within a single reading frame.

Preparation of the subject nucleic acids can be carried out by a variety of routine recombinant techniques and synthetic procedures. Standard recombinant DNA and molecular cloning techniques are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987). Briefly, the subject nucleic acids can be prepared genomic DNA fragments, cDNAs, and RNAs, all of which can be extracted directly from a cell or recombinantly produced by various amplification processes including but not limited to PCR and rt-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (for example, Matteuci et al., *Tet. Lett.* 521:719 (1980); U.S. Pat. No. 4,500,707 to Caruthers et al.; and U.S. Pat. Nos. 5,436,327 and 5,700,637 to Southern et al.).

Regulatory elements include, for example, promoters and operators, which can also be engineered to increase the expression of one or more heterologous sequences encoding a glycoprotein. A promoter is a sequence of nucleotides that initiates and controls the transcription of a nucleic acid sequence by an RNA polymerase enzyme. An operator is a sequence of nucleotides adjacent to the promoter that functions to control transcription of the desired nucleic acid sequence. The operator contains a protein-binding domain where a specific repressor protein can bind. In the absence of a suitable repressor protein, transcription initiates through the promoter. In the presence of a suitable repressor protein, the repressor protein binds to the operator and thereby inhibits transcription from the promoter.

In some embodiments of the present disclosure, promoters used in expression vectors are inducible. In other embodiments, the promoters used in expression vectors are constitutive. In some embodiments, one or more nucleic acid sequences are operably linked to an inducible promoter, and one or more other nucleic acid sequences are operably linked to a constitutive promoter. Non-limiting examples of suitable promoters for use in eukaryotic host cells include, but are not limited to, a CMV immediate early promoter, an HSV thymidine kinase promoter, an early or late SV40 promoter, LTRs from retroviruses, and a mouse metallothionein-I promoter.

The genes in the expression vector typically will also encode a ribosome binding site to direct translation (that is, synthesis) of any encoded mRNA gene product. Other regulatory elements that may be used in an expression vector include transcription enhancer elements and transcription terminators. See, for example, Bitter et al., Methods in Enzymology, 153:516-544 (1987).

An expression vector may be suitable for use in particular types of host cells and not others. One of ordinary skill in the art, however, can readily determine through routine experimentation whether a particular expression vector is suited for a given host cell. For example, the expression vector can be introduced into the host organism, which is then monitored for viability and expression of any genes contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other transformation methods include microinjection, DEAE dextran mediated transformation, and heat shock in the presence of lithium acetate. Lipid complexes, liposomes, and dendrimers may also be employed to transfect the host cells.

Upon introduction of the heterologous sequence into a host cell, a variety of methods can be practiced to identify the host cells into which the subject vectors have been introduced. One exemplary selection method involves subculturing individual cells to form individual colonies, followed by testing for expression of the desired protein product. Another method entails selecting host cells containing the heterologous sequence based upon phenotypic traits conferred through the expression of selectable marker genes contained within the expression vector. Those of ordinary skill can identify genetically modified host cells using these or other methods available in the art.

For example, the introduction of various heterologous sequences of the disclosure into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reveres-transcription coupled PCR, Northern blot hybridization, or by immunoassays using antibodies reactive with the encoded gene product. Exemplary immunoassays include but are not limited to ELISA, radioimmunoassays, and sandwich immunoassays.

Furthermore, the introduction of various heterologous sequences of the disclosure into a host cell can be confirmed by the enzymatic activity of an enzyme that the heterologous sequence encodes. The enzyme can be assayed by a variety of methods known in the art. In general, the enzymatic activity can be ascertained by the formation of the product or conversion of a substrate of an enzymatic reaction that is under investigation. The reaction can take place in vitro or in vivo.

In another aspect, the invention provides a method of producing a fusion polypeptide to achieve desired pharmacokinetic, pharmacologic or pharmaceutical properties. In some cases, the fusion polypeptide can be produced by expressing a vector in a cell under conditions suitable for protein expression.

The suitable conditions for protein expression, including but not limited to factors such as incubation time, temperature, and medium, may be dependent on cell type and will be readily determined by one of ordinary skill in the art.

Methods of Treatment

In one aspect, the invention provides methods of using the fusion polypeptides of the present invention to treat disease conditions in a mammal, including but not limited to conditions implicated by interferon lambda receptor (IFNλR1 and/or IL10R2) malfunction.

In some cases, the present invention provides a method of treating a viral infection in a mammal in need thereof, comprising administering to the mammal a therapeutically effective amount of a fusion polypeptide of the invention. In some examples, the viral infection can be inflicted by hepatitis B or hepatitis C. In other examples, the viral infection can be inflicted by influenza. Further examples of viral infection include but are not limited to human lymphotropic virus-type 1 (HTLV-1) and human papilloma virus (HPV).

In other cases, the present invention provides a method of treating an inflammatory disorder in a mammal in need thereof, comprising administering to the mammal a therapeutically effective amount of a fusion polypeptide of the invention. In some cases, the inflammatory disorder can be multiple sclerosis. In other cases, the inflammatory disorder can be an autoimmune disease. Examples of autoimmune diseases include but are not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barre syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In further cases, the present invention provides a method of treating cancer in a mammal in need thereof, comprising administering to the mammal a therapeutically effective amount of a fusion polypeptide of the invention. In some cases, the cancer can be hepatocellular carcinoma. In other cases, the cancer can be acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related (e.g. Lymphoma and Kaposi's Sarcoma) or Viral-Induced cancer.

Additionally, the fusion polypeptides described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

In some cases, the mammal is a human. In other cases, the mammal can be a mouse, a rat, a cat, a dog, a rabbit, a pig, a sheep, a horse, a bovine, a goat, a gerbil, a hamster, a guinea pig, a monkey or any other mammal. many such mammals may be subjects that are known to the art as preclinical models for certain diseases or disorders, including solid tumors and/or other cancers (e.g., Talmadge et al., 2007 Am. J. Pathol. 170:793; Kerbel, 2003 Canc. Biol. Therap. 2(4 Suppl 1):S134; Man et al., 2007 Canc. Met. Rev. 26:737; Cespedes et al., 2006 Clin. TransL Oncol. 8:318).

In another aspect, the invention provides methods of using the fusion polypeptides of the present invention to treat disease conditions in a mammal wherein the fusion polypeptides may be formulated or administered in conjunction with a second agent. In some cases, the second agent can be an antiviral agent. These agents include but are not limited to telaprevir, boceprevir, semiprevir, sofosbuvir, daclastavir, asunaprevir, lamivudine, adefovir, entecavir, tenofovir, telbivudine, interferon alpha and PEGylated interferon alpha. In other cases, the second agent can be an agent that acts to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In further cases, the agent can be an anti-cancer agent (e.g. a chemotherapeutic agent). The chemotherapeutic can be selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples of chemotherapeutic agents, cytotoxic agents, and non-peptide small molecules include but are not limited to GLEEVEC® (Imatinib Mesylate), VELCADE® (bortezomib), CASODEX (bicalutamide), TRESSA® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, CASODEX™ (bicalutamide), chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulene Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (NOLVADEX™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the fusion polypeptides of the present invention can be used in combination with commonly prescribed anti-cancer drugs such as HERCEPTIN®, AVASTIN®, ERBITUX®, RITUXAN®, TAXOL®, ARIMIDEX®, TAXOTERE®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

Pharmaceutical Compositions

A pharmaceutical composition of the invention typically contains an active ingredient (e.g., a fusion polypeptide, a PEG-modified fusion polypeptide) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants. Described below are non-limiting exemplary pharmaceutical compositions and methods for preparing the same.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition can further comprise a fusion polypeptide and/or a PEG-modified fusion polypeptide according to the invention as an active ingredient and may include a conventional pharmaceutical carrier or excipient. Further, it may include other medicinal or pharmaceutical agents, carriers, adjuvants, etc.

Exemplary parenteral administration forms include solutions or suspensions of active polypeptide and/or PEG-modified polypeptide in sterile aqueous solutions, for example, aqueous propylene glycol or dextrose solutions. Such dosage forms can be suitably buffered with salts such as histidine and/or phosphate, if desired.

In some cases, the invention provides a pharmaceutical composition for injection containing a polypeptide or a PEG-modified polypeptide of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the polypeptide and/or PEG-modified polypeptide of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some cases, the invention provides a pharmaceutical composition for oral administration containing a fusion polypeptide and/or PEG-modified fusion polypeptide of the invention, and a pharmaceutical excipient suitable for oral administration.

In some cases, the invention provides a solid pharmaceutical composition for oral administration containing: (i) an effective amount of a polypeptide or a PEG-modified polypeptide of the invention; optionally (ii) an effective amount of a second agent; and (iii) a pharmaceutical excipient suitable for oral administration. In some embodiments, the composition further contains: (iv) an effective amount of a third agent.

In some cases, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

This invention further encompasses anhydrous pharmaceutical compositions and dosage forms comprising an active ingredient, since water can facilitate the degradation of some polypeptides. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A fusion polypeptide can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

D3 Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters;

sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, 6-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The examples and preparations provided below further illustrate and exemplify the fusion polypeptides of the present invention and methods of using and preparing thereof. It is to be understood that the scope of the present invention is not limited in any way by the scope of the following examples and preparations.

Example 1: Cloning and expression of IL28B/IL29 fusion polypeptides

Figure 2:
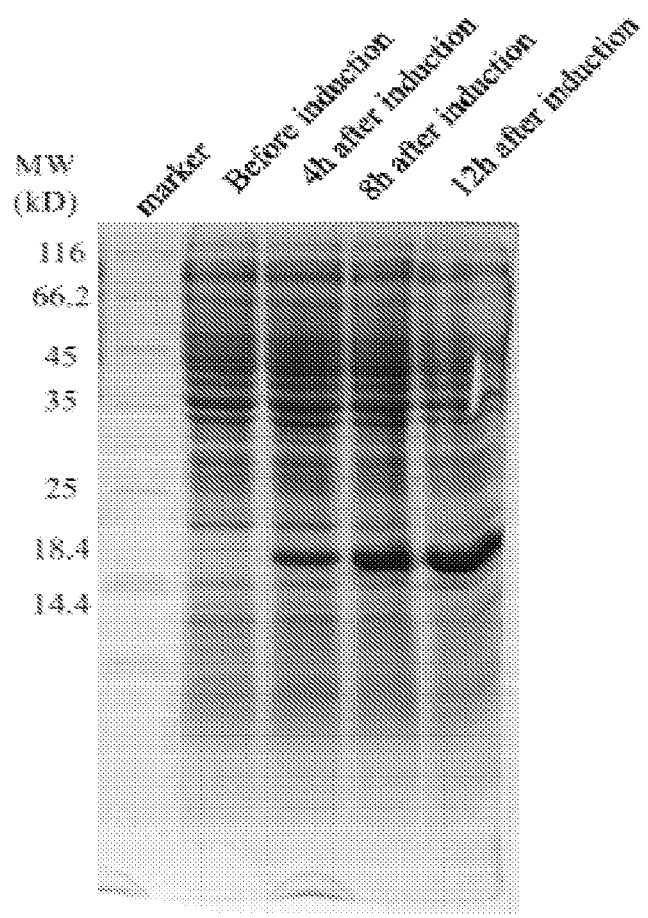
FIG. 2 illustrates the SDS-PAGE analysis following the protein expression of a fusion polypeptide (SEQ ID NO: 12) using the methods of the present invention.

Fusion polypeptides of SEQ ID NO: 1, 2, 3, 4, 5, 6, 7, 8, 9, 10, 11, 12, 13, 14, 15, 16, 17, 18, and 19 were designed and expressed in E. coli. Briefly, genes encoding the fusion polypeptides were inserted into the expression vector pET11c between the Nde1 and BamH1 restriction sites and expression was conducted under control of the phage T7 promotor. The vectors were transformed into E. coli BL21 (DE3). The cells were grown in LB media supplemented with 100 µg/ml of ampicillin to $OD_{450}$ of 0.4-0.6. Expressions were induced by addition of 1 mM IPTG for 12 hours at 37° C. Cells were harvested by centrifugation, suspended in PBS, and sonicated. The cell homogenates were centrifuged. SDS-PAGE analysis was performed to demonstrate that fusion polypeptides, for example SEQ ID NO: 8 and SEQ ID NO: 12, were successfully expressed in the insoluble inclusion body fractions (FIGS. 1 & 2, respectively).

Example 2: Refolding and Purification of IL28B/IL29 Fusion Polypeptides

Figure 3:
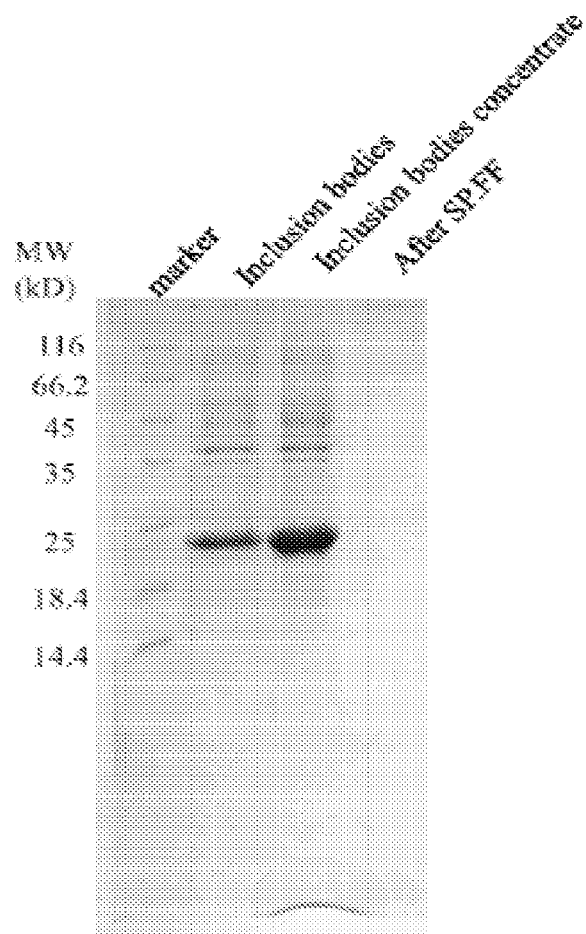
FIG. 3 illustrates the SDS-PAGE analysis following the refolding and purification of a fusion polypeptide (SEQ ID NO: 8) using the methods of the present invention.
Figure 4:
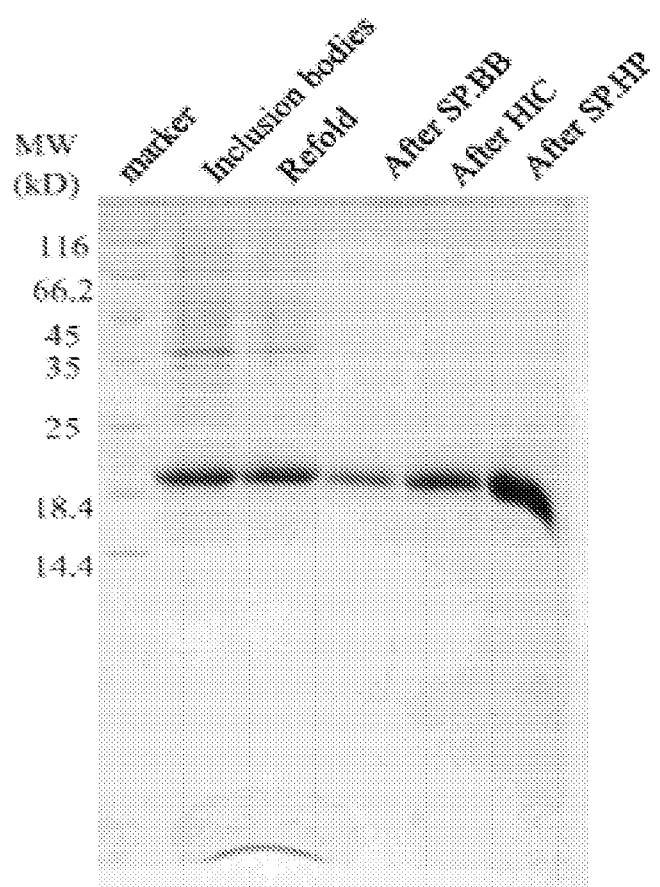
FIG. 4 illustrates the SDS-PAGE analysis following the refolding and purification of a fusion polypeptide (SEQ ID NO: 12) using the methods of the present invention.

Fusion polypeptides of SEQ ID NO: 1, 3, 5, 7, 9, 11, 12, 13, 14, 15, 16, and 17 were refolded and purified as follows. Inclusion body pellets were solubilized in 50 mM Tris pH 8.0, 6 M guanidine, 10 mM DTT and clarified by centrifugation. The solubilized inclusion body were then dialyzed (MWCO: 3000) against 50 mM Tris pH 7.8, 1 M arginine, 2 mM GSH, 1 mM GSSG at 4° C. overnight. The refolded fusion polypeptides were purified by cation exchange chromatography (50 mM NaOAc, pH 5.5, 0-1 M NaCl) using SP BB (GE Healthcare), followed by hydrophobic interaction chromatography (50 mM NaOAc, 1-0 M $(NH_4)_2SO_4$) using Butyl Sepharose Fast Flow resin (GE Healthcare). Further purification was achieved by cation exchange chromatography (50 mM NaOAc, pH 5.5, 0-1 M NaCl) using SP HP resin (GE Healthcare). SDS-PAGE analysis was performed and demonstrated that in some cases the fusion polypeptides (e.g. SEQ ID NO: 8) did not yield visible purified protein by this method (FIG. 3), whereas in other cases the fusion polypeptides (e.g. SEQ ID NO: 12) were successfully refolded and purified (FIG. 4).

Example 3: PEGylation of IL28B/IL29 Fusion Polypeptides at the N-Terminus

Purified fusion polypeptide of SEQ ID NO: 3 was concentrated to 1 mg/mL and buffered exchanged into 50 mM NaOAc, pH 5.5, 10 mM $NaCNBH_3$. Monomethoxy PEG propionaldehyde (20 Kd, NOF) was added (5 molar equivalents to the IL28B analogue) and the reaction mixture was incubated at room temperature overnight. The resulting PEGylated fusion polypeptide (Compound A) was then purified by cation exchange chromatography (50 mM NaOAc, pH 5.5, 0-1 M NaCl) using SP HP (FIG. 5).

Figure 5:
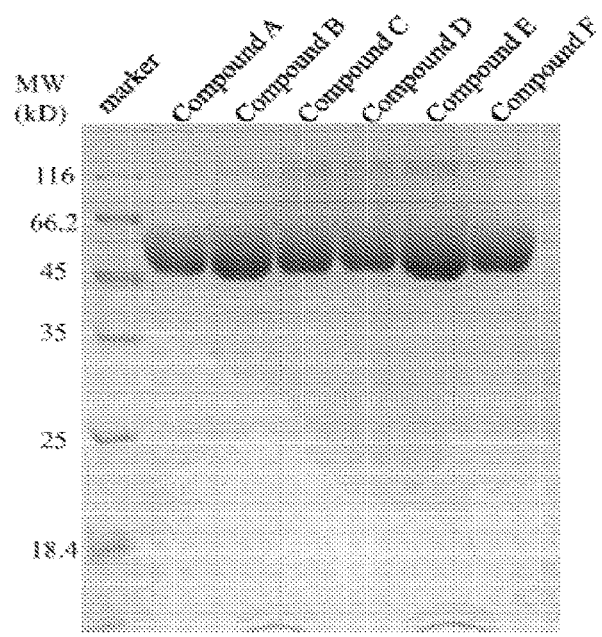
FIG. 5 illustrates the SDS-PAGE analysis following the N-terminal PEGylation and SP-HP purification of fusion polypeptides (SEQ ID NO: 3, SEQ ID NO: 5, SEQ ID NO: 7, SEQ ID NO: 11, SEQ ID NO: 12 and SEQ ID NO: 13) using the methods of the present invention.

Fusion polypeptides of SEQ ID NO: 5, SEQ ID NO: 7, SEQ ID NO: 11, SEQ ID NO: 12 and SEQ ID NO: 13 were each PEGylated at the N-terminus with a 20 Kd monomethoxy PEG using the method described above to yield Compound B, Compound C, Compound D, Compound E and Compound F, respectively (FIG. 5).

Example 4: PEGylation of IL28B/IL29 Fusion Polypeptides at the Cysteine Thiol Moiety Purified fusion polypeptide of SEQ ID NO: 14 was concentrated to 1 mg/mL and buffered exchanged into PBS at pH 7.0. Monomethoxy PEG maleimide (20 Kd, NOF) was added (20 molar equivalents to fusion polypeptide) and the reaction mixture was incubated at 4° C. overnight. The fusion polypeptide was thereby PEGylated at the thiol moiety of C168 to yield Compound G, which was then purified by cation exchange chromatography (50 mM NaOAc, pH 5.5, 0-1 M NaCl) using SP HP (FIG. 6).

Figure 6:
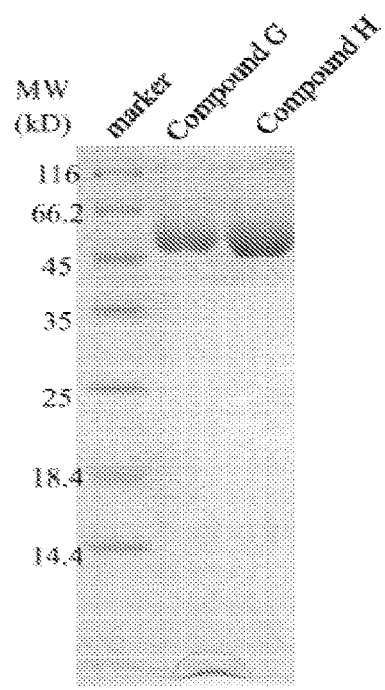
FIG. 6 illustrates the SDS-PAGE analysis following PEGylation of fusion polypeptides (SEQ ID NO: 14 and SEQ ID NO: 15) at the C168 thiol moiety.

PEGylation of SEQ ID NO: 15 was similarly performed to yield compound H (FIG. 6).

Example 5: Induction of Interferon-Stimulated Genes by IL28B/IL29 Fusion Polypeptides The antiviral effects of the IL28B/IL29 fusion polypeptides were assessed in antiviral gene-induction assay. The assay measured induction of interferon-stimulated genes (ISG) in Hep G2 cells (ATCC HB-8065) after addition of the IL28B/IL29 fusion polypeptides. Hep G2 cells were plated in 6-well plates in complete DMEM media at a concentration of $5 \times 10^5$ cells/well. Twenty-four hours after plating cells, drug treatment was initiated by replacing cell culture media with new media containing a test protein at a concentration of 0.1 ng/ml, 1 ng/ml, 10 ng/ml or 100 ng/ml. Cells were harvested at 3, 12, 24, 48 or 72 hours after initiation of drug treatment. As controls, cells were either stimulated with human IFNα (PeproTech, 300-02AB) or IL-29 (SEQ ID NO: 1) positive controls, or unstimulated negative control. All treatments were performed in triplicates.

The cells were then analyzed for viability with an MTT assay, which showed that drug treatment caused no impact on the growth and viability of the cell. Total RNA was isolated from cell pellets and treated with RNase-free DNase. 2 µg of total RNA was used as the template for cDNA synthesis using PrimeScript RT Master Mix (Takara, RR036) and oligo(dT) as the primer. ISG gene-induction was evaluated by real-time PCR using SYBR Premix Ex Taq (Takara, RR820) on the LightCycler 480 (Roche Applied Science). Each PCR reaction was run in triplicates and the average value was used for calculation. Data shown was normalized to GAPDH or f-actin and shown as fold induction over unstimulated cells.

1. Dose-Dependence

Figure 7:
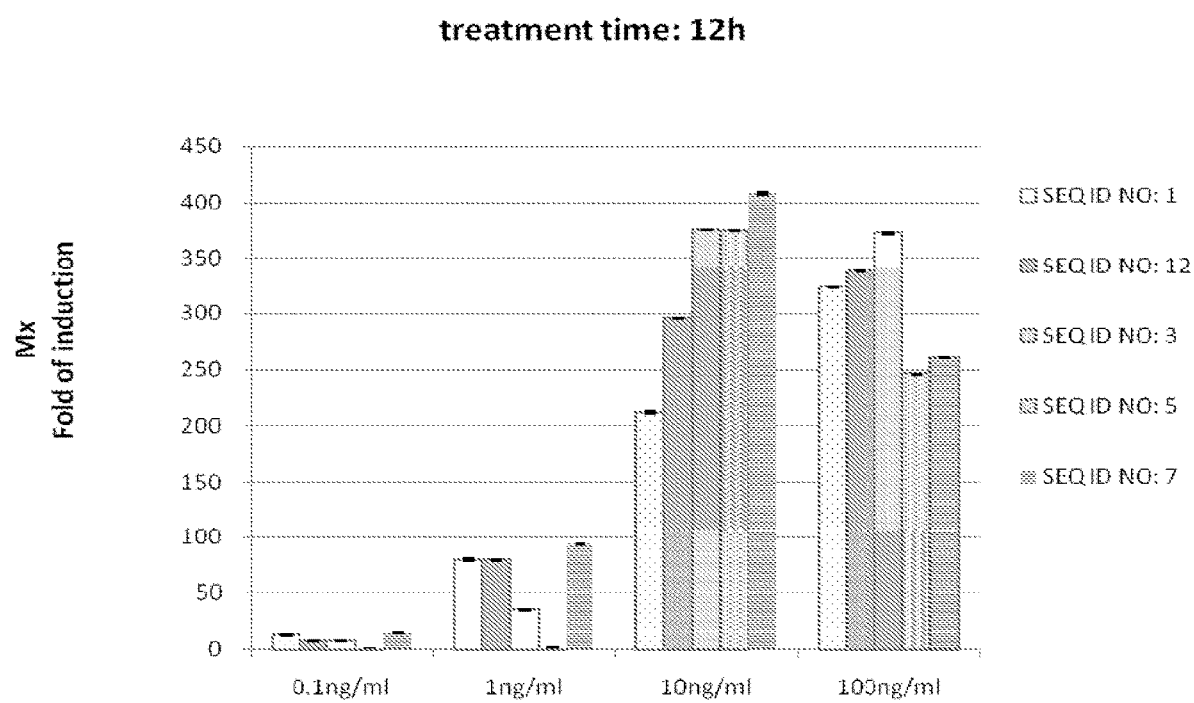
FIG. 7 illustrates the dose-dependent induction of Mx in Hep G2 cells at 12 hours after treatment with reference IL29 protein (SEQ ID NO: 1) and four IL28B/IL29 fusion polypeptides (SEQ ID NO: 3, SEQ ID NO: 5, SEQ ID NO: 7, and SEQ ID NO: 12).
Figure 8:
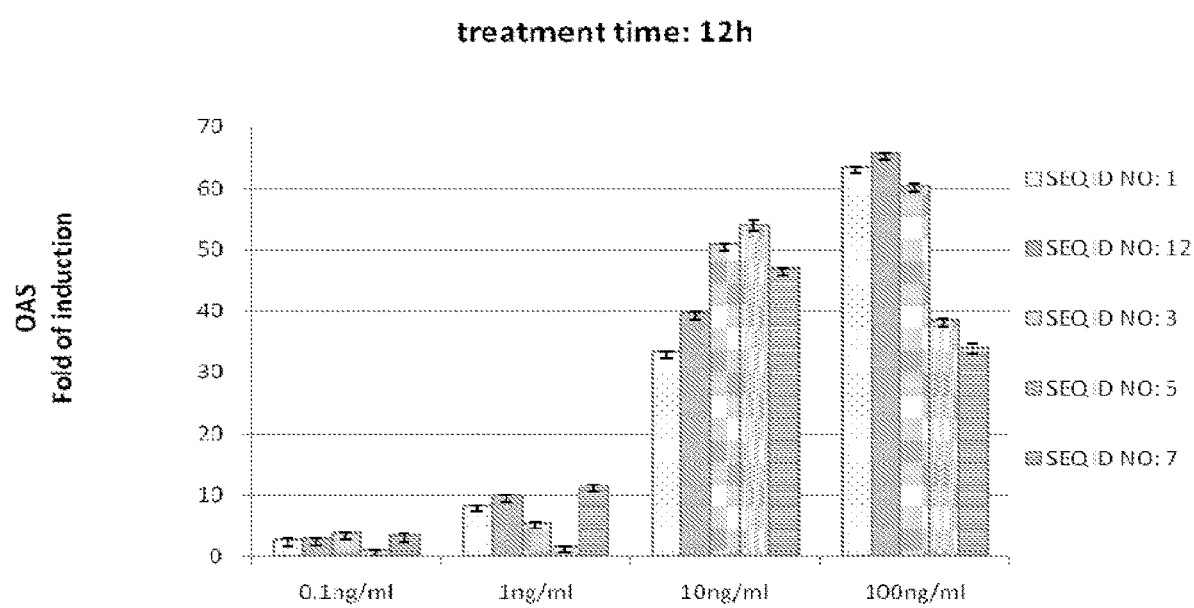
FIG. 8 illustrates the dose-dependent induction of OAS in Hep G2 cells at 12 hours after treatment with reference IL29 protein (SEQ ID NO: 1) and four IL28B/IL29 fusion polypeptides (SEQ ID NO: 3, SEQ ID NO: 5, SEQ ID NO: 7, and SEQ ID NO: 12).

As an example, at 12 hours after initiation of treatment, reference IL-29 peptide (SEQ ID NO: 1) and 4 IL-28B/IL-29 fusion polypeptides (SEQ ID NO: 3, 5, 7, and 12) all showed marked, dose-dependent induction of Mx and OAS in Hep G2 cells (FIGS. 7 & 8, respectively). At concentrations of 10 ng/ml or higher, the Mx expression increased 200-400 fold and the OAS levels increased by 30-60 fold. Further, the IL-28B/IL-29 fusion polypeptides were shown to induce antiviral gene expression at levels comparable or slightly higher than the reference IL-29 protein.

2. Time-Dependence

Figure 9:
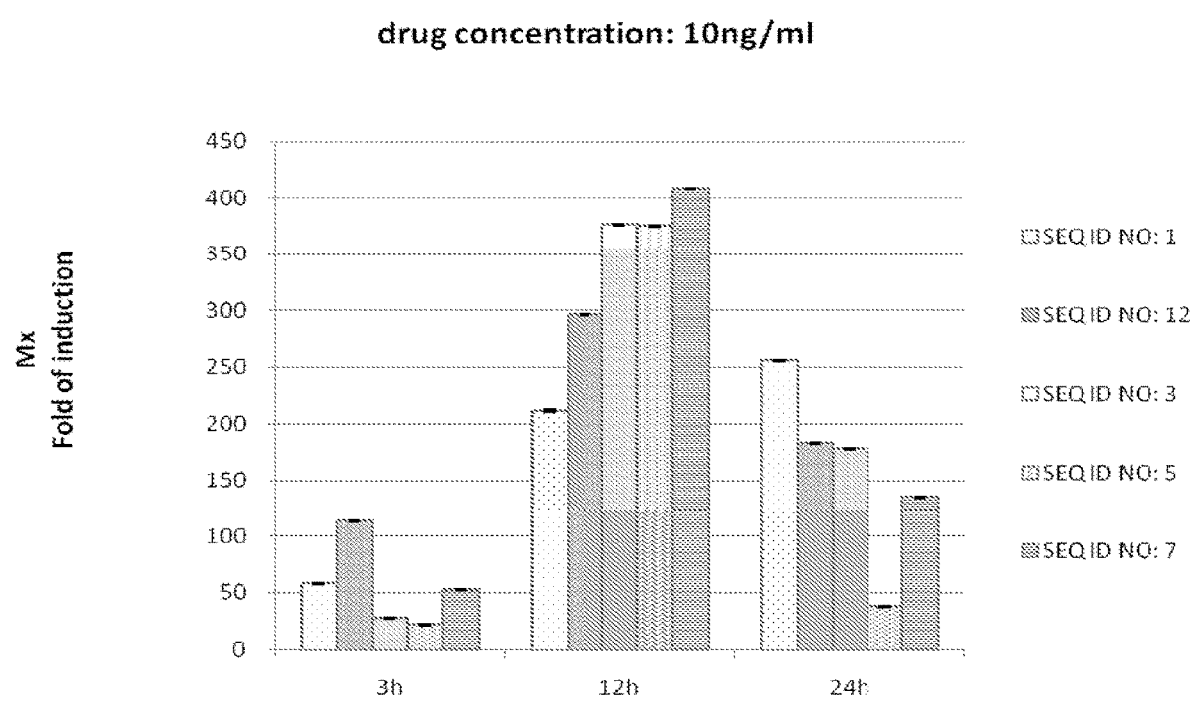
FIG. 9 illustrates the time-dependent induction of Mx in Hep G2 cells after treatment with 10 ng/mL of n reference IL29 protein (SEQ ID NO: 1) and four IL28B/IL29 fusion polypeptides (SEQ ID NO: 3, SEQ ID NO: 5, SEQ ID NO: 7, and SEQ ID NO: 12).
Figure 10:
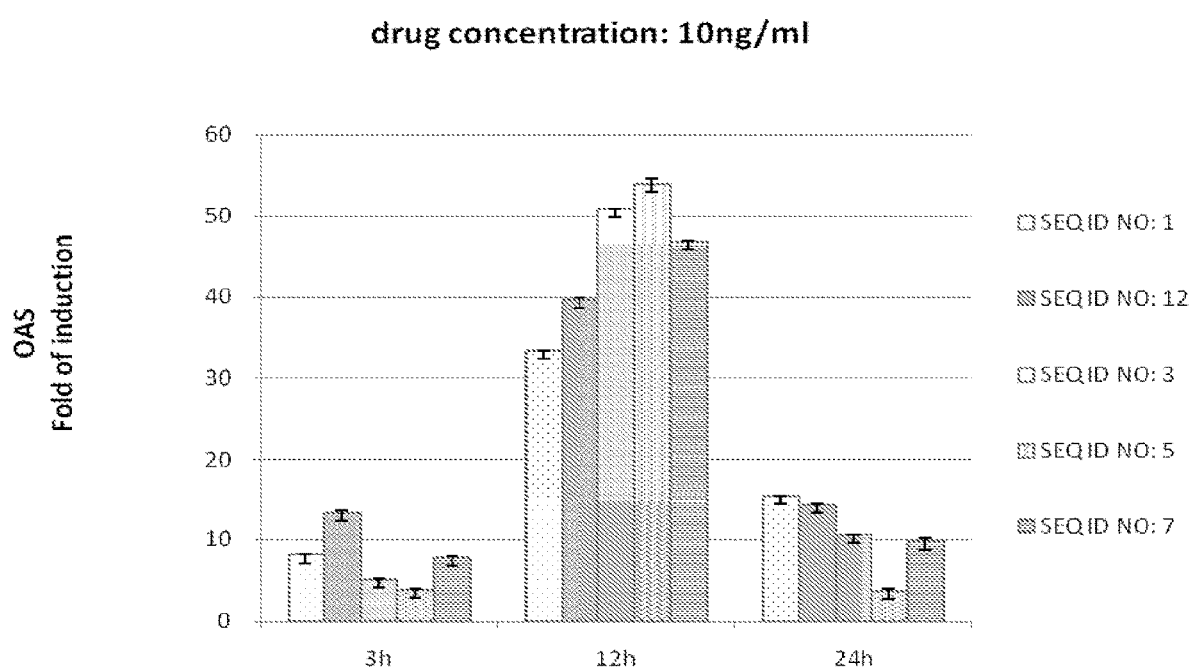
FIG. 10 illustrates the time-dependent induction of OAS in Hep G2 cells after treatment with 10 ng/mL of reference IL29 protein (SEQ ID NO: 1) and four IL28B/IL29 fusion polypeptides (SEQ ID NO: 3, SEQ ID NO: 5, SEQ ID NO: 7, and SEQ ID NO: 12).

Induction of Mx and OAS expression was observed after drug treatment for 3 hours, where the highest induction was reached after 12 hours (FIGS. 9 & 10, respectively).

3. Mx, OAS-Induction Activity is Lost when the Analogues are Denatured

Figure 11:
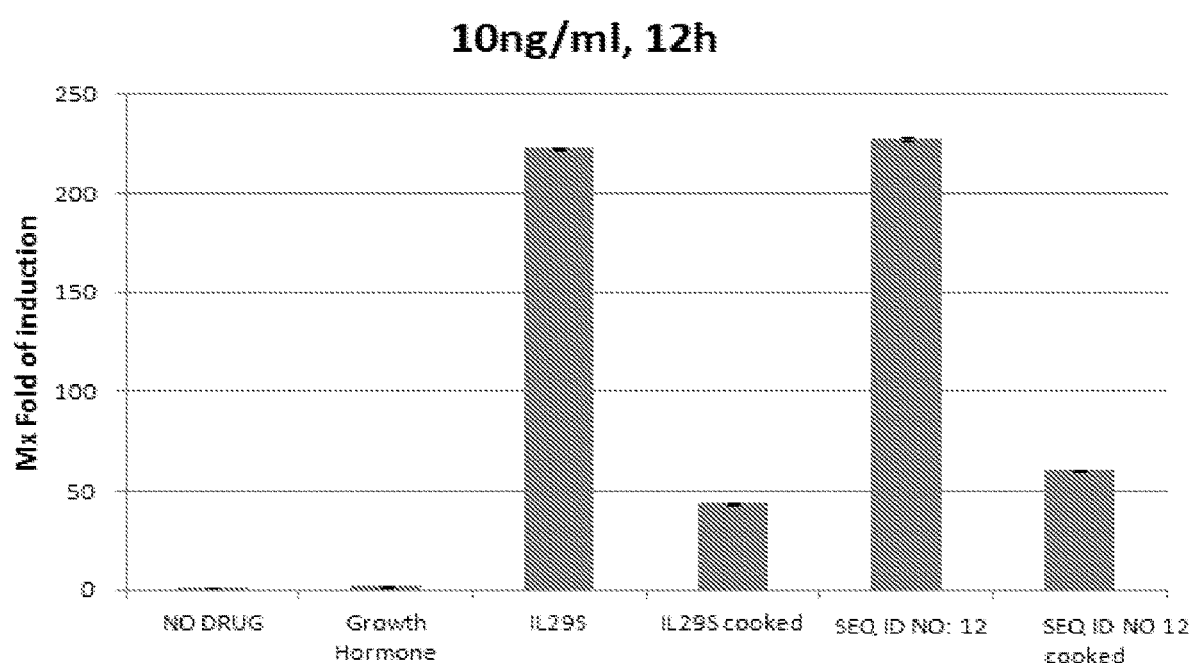
FIG. 11 illustrates the loss in Mx-induction following denaturation of the reference IL29 (SEQ ID NO: 1) and IL28B/IL29 fusion polypeptide (SEQ ID NO: 12).
Figure 12:
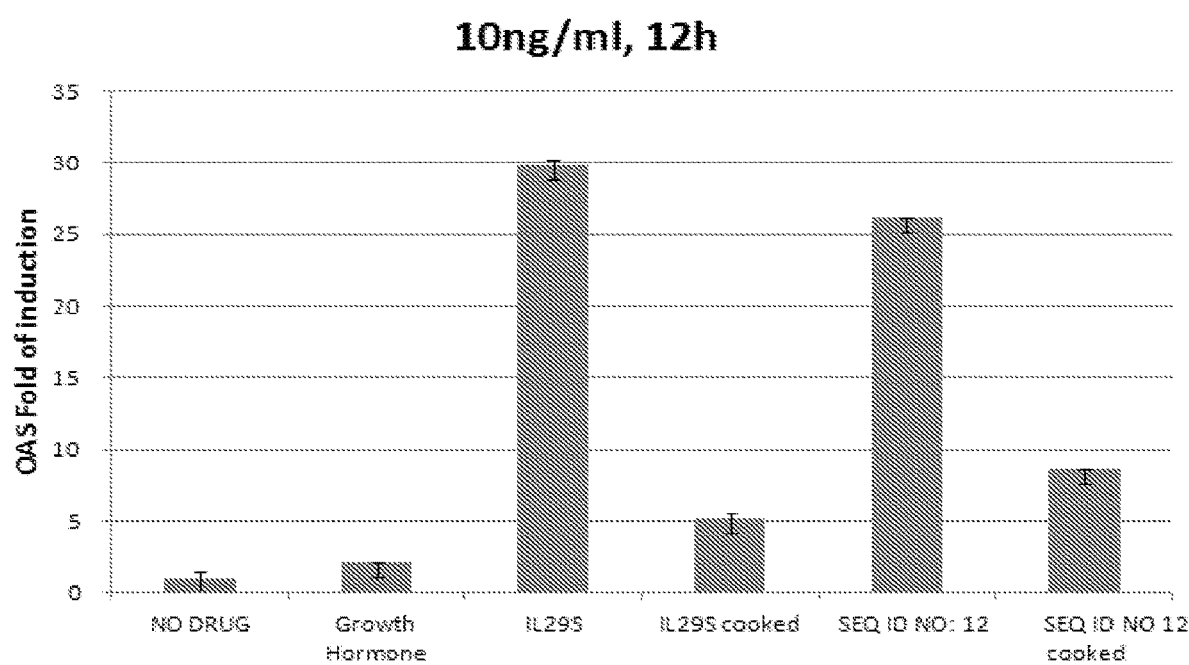
FIG. 12 illustrates the loss in OAS-induction following denaturation of the reference IL29 (SEQ ID NO: 1) and IL28B/IL29 fusion polypeptide (SEQ ID NO: 12).

To confirm the effects observed in the experiments above, the IL-28B/IL-29 fusion polypeptides were denatured by cooking at 95° C. for 5 min. Recombinant human growth hormone was used as a negative control in the repeat experiments. The results show that the antiviral gene-induction was greatly reduced when the IL-28B/IL-29 fusion polypeptides were first denatured, whereas no significant effect on Mx and OAS expression was seen with recombinant human growth hormone, indicating that the activity seen in the experiments above was inherent to the IL-28B/IL-29 fusion polypeptides (FIGS. 11 & 12, respectively).

4. PEGylated IL-28B/IL-29 Fusion Polypeptides Show Similar Biological Activity

Figure 13:
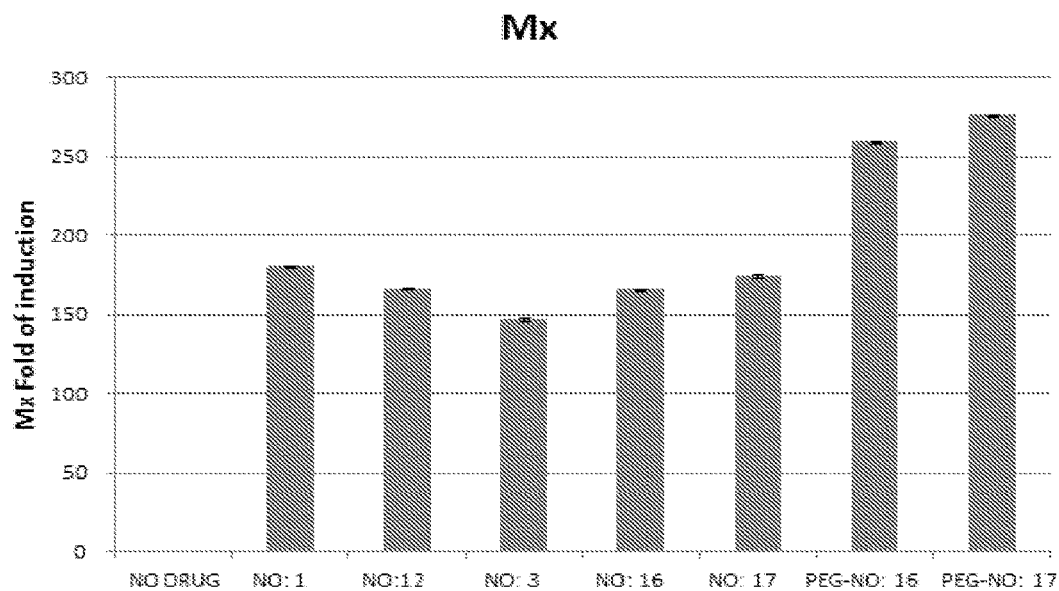
FIG. 13 illustrates the Mx induction properties of reference IL29 peptide (SEQ ID NO: 1), fusion polypeptides of IL28B/IL29 (SEQ ID NO: 12 and SEQ ID NO: 3), modified fusion polypeptides of IL28B/IL29 (SEQ ID NO: 16 and SEQ ID NO:17), and N-terminal PEGylated modified fusion polypeptides of IL28B/IL29 (SEQ ID NO: 16 and SEQ ID NO:17).
Figure 14:
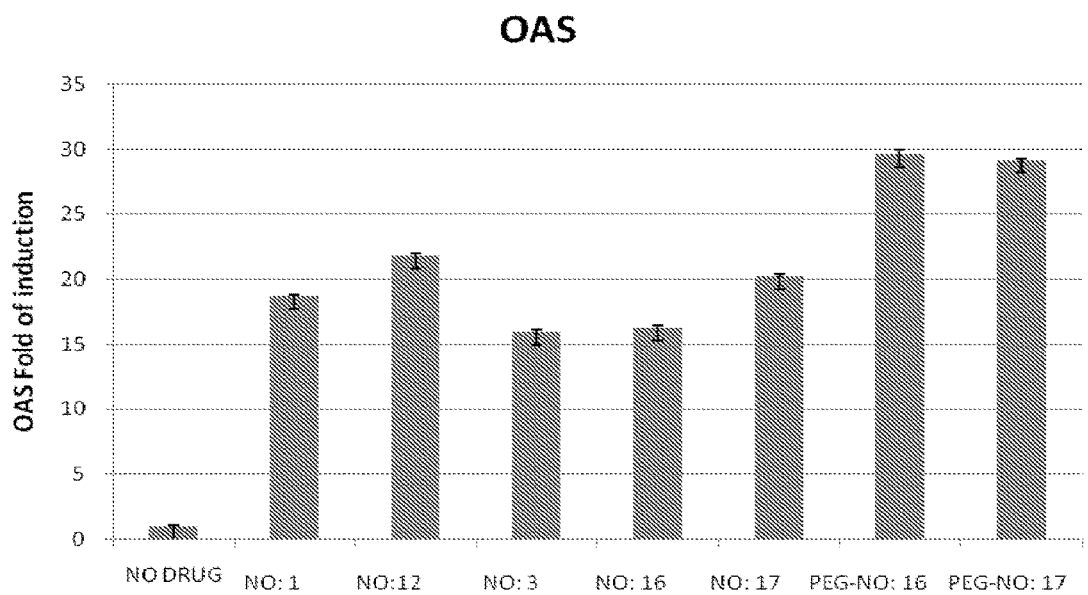
FIG. 14 illustrates the Mx induction properties of reference IL29 peptide (SEQ ID NO: 1), fusion polypeptides of IL28B/IL29 (SEQ ID NO: 12 and SEQ ID NO: 3), modified fusion polypeptides of IL28B/IL29 (SEQ ID NO: 16 and SEQ ID NO:17), and N-terminal PEGylated modified fusion polypeptides of IL28B/IL29 (SEQ ID NO: 16 and SEQ ID NO:17).

PEGylated IL-28B/IL-29 fusion polypeptides were further tested and shown to possess similar antiviral gene-inducing activity as compared to the unmodified polypeptides (FIGS. 13 & 14, respectively).

Example 6: Inhibition of HCV Replication in Huh-7.5.1 Cells by PEGylated IL-28B/IL-29 Fusion Polypeptides HCV is a single-stranded, positive-sense RNA virus, which does not replicate in conventional cell cultures due to its restricted tropism. Development of infection system using cell-culture-derived infectious HCV (HCVcc) has greatly helped the study of the complete viral replication cycle as well as drug discovery efforts relative to the entire infectious virus life cycle.

To test the ability of PEGylated IL-28B/IL-29 fusion polypeptides to inhibit HCV replication, genotype 2a HCV genomic RNA was transcribed in vitro from the plasmid pJFH-1, and used to transfect Huh-7.5.1 cells. HCVcc was harvested from the supernatant of cell culture media, and high-titered viral stock was generated by propagation in Huh-7.5.1 cells. To determine the viral titer (focus-forming units, FFU/ml), Huh-7.5.1 cells were seeded in 8-well chamber slides at $2\times10^4$ cells/well, infected with different amount of viral stock solution, and the number of positive foci was counted following immunostaining using anti-HCV Core Antigen (Pierce Antibodies, Thermo Scientific, Clone C7-50, MA1-080).

Figure 15:
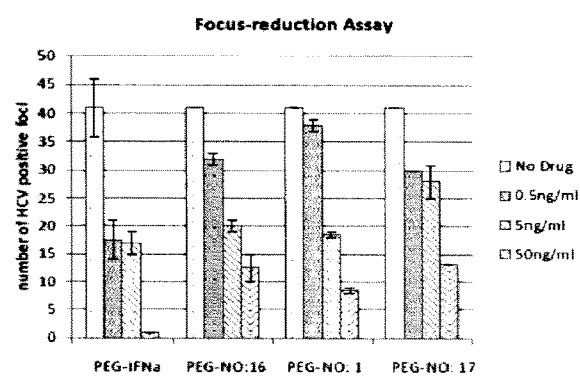
FIG. 15 illustrates the HCV replication inhibition properties of PEGylated interferon a2b (Pegasys), reference N-terminal PEGylated IL29 peptide (SEQ ID NO:1), N-terminal PEGylated modified IL28B/IL29 fusion polypeptide (SEQ ID NO:16), and N-terminal PEGylated modified IL28B/IL29 fusion polypeptide (SEQ ID NO:17).

For in vitro drug efficacy testing, Huh-7.5.1 cells were plated in 8-well chamber slides in complete DMEM media at a density of $2\times10^4$ cells/well. 24 hours later, cells were infected by JFH-1 HCVcc at 0.1×M.O.I., and 4 hours later, drug treatment was initiated by replacing cell culture media with new media containing a test protein at a concentration of 0 ng/ml, 1 ng/ml, 10 ng/ml or 100 ng/ml; culture media were changed daily with new media containing the same test protein. All treatments were performed in triplicates. Cells were immunostained against HCV core antigen after initiation of drug treatment for 48 hours. All positive foci in each well were counted under a fluorescent microscope using a 10× objective lens. The results showed that comparing to PEG-IFNα and reference PEG-IL-29 (SEQ ID NO: 1), the derivatives PEG-NO: 16 (N-terminus 20K pegylated SEQ ID NO: 16) and PEG-NO: 17 (N-terminus 20K pegylated SEQ ID NO 17) were similarly potent in inhibiting HCV replication (FIG. 15).

Example 7: IL-28A/IL29 Fusion Polypeptides Inhibit Influenza a Viral Replication in A549 Cells The ability of the IL-28B/IL29 fusion polypeptides to inhibit replication of influenza viruses was tested in H3N2-infected A549 cells (human adenocarcinomic alveolar basal epithelial cells). A549 cells were pre-treated with a test protein for 24 hours, and then infected with H3N2 viruses for 90 min; 72 hours later, cells were fixed and immunostained with an anti-NP antibody, followed by anti-mouse HRP; drug efficacy was evaluated by ELISA measuring readings of each well at OD490 nm.

A549 cells were plated in 96-well plates in complete DMEM media at a concentration of $3\times10^4$ cells/well. Twenty-four hours after plating cells, cell culture media was replaced with new media containing a test protein at a concentration of 0.5 ng/ml, 5 ng/ml, 50 ng/ml or 500 ng/ml. Twenty-four hours later, cell culture media was replaced with new media containing 30×TCID 50/50 µl H3N2 (A3/Brisbane) virus. After 90 min, cell culture media was replaced with new media without virus. As controls, cells were either uninfected and untreated (CV) or infected and untreated (VV). All treatments were performed in triplicates. IFNa2b, reference IL29 (SEQ ID NO: 1), SEQ ID NO: 17, N-terminus 20K PEGylated fusion polypeptide SEQ ID NO: 16 (PEG-NO:16), and N-terminus 20K PEGylated fusion polypeptide SEQ ID NO: 17 (PEG-NO:17), as well as CV and VV were tested (FIG. 16).

Figure 17:
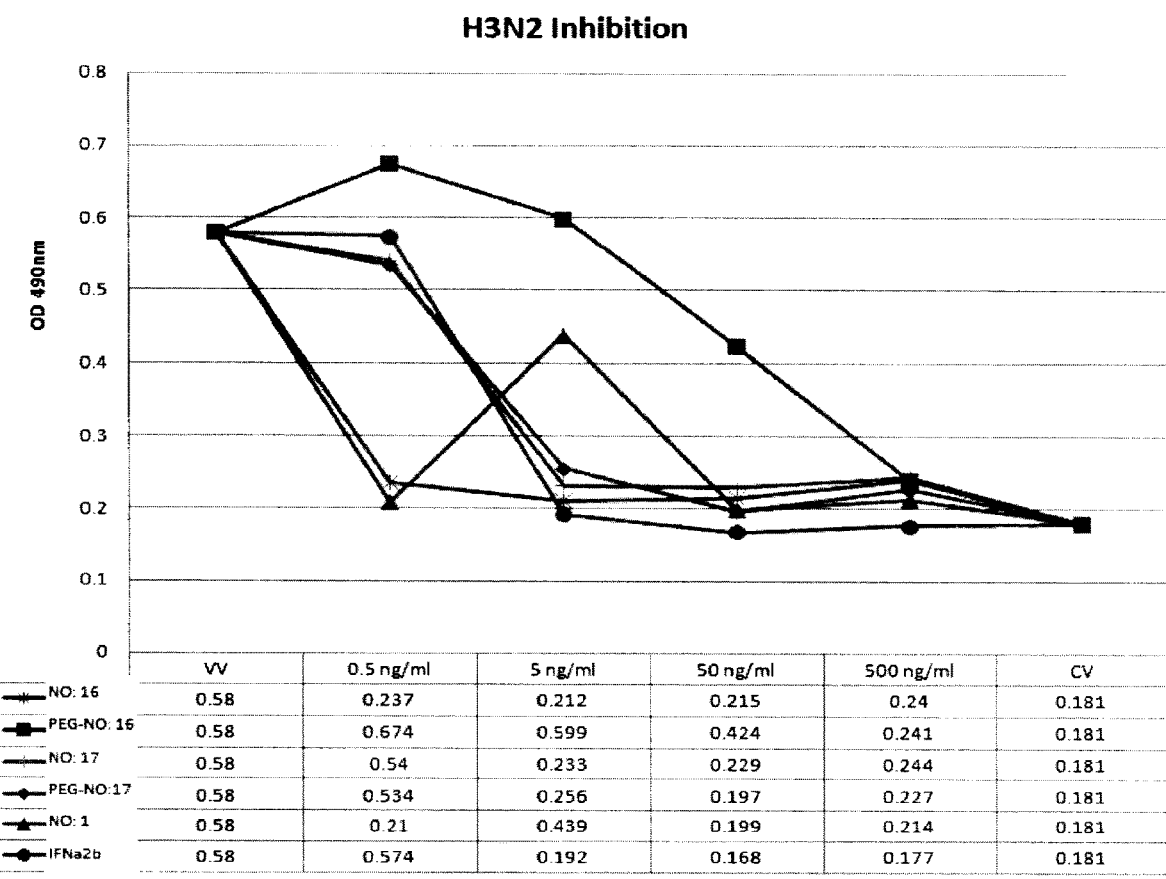
FIG. 17 illustrates inhibition of H3N2 infection of the A549 cells following the various treatment conditions.

72 hours after initiation of viral infection, cells were fixed by ice-cold acetone, immunostained by mouse anti-NP monoclonal antibody, followed by rabbit-anti-mouse-HRP. OD490 nm of each well was scored using a plate reader. The results indicated that the IL28B/IL29 fusion polypeptides SEQ ID NO: 16 and SEQ ID NO: 17, as well as their respective N-terminus 20K PEGylated derivatives were effective in inhibiting influenza viral replication (FIG. 17).

Sequence Listing

```
SEQ ID NO 1:
MKPTTTGKGCHIGRFKSLSPQELASFKKARDALEESLKLKNWSCSSPVFPGNWDLRLLQVR

ERPVALEAELALTLKVLEAAAGPALEDVLDQPLHTLHHILSQLQACIQPQPTAGPRPRGRLH

HWLHRLQEAPKKESAGCLEASVTFNLFRLLTRDLKYVADGNLSLRTSTHPEST

SEQ ID NO 2:
MVPVARLRGALPDARGCHIAQFKSLSPQELQAFKRAKDALEESLLLKDSKCRSRLFPRTWD

LRQLQVRERPVALEAELALTLKVLEATADTDPALGDVLDQPLHTLHHILSQLRACIQPQPTA

GPRTRGRLHHWLHRLQEAPKKESPGCLEASVTFNLFRLLTRDLNSVASGDLSV
```

SEQ ID NO 3:
MKPTTTGKGCHIGRFKSLSPQELASFKKARDALEESLKLKNWSCSSPVFPGNWDLRLLQVR

ERPVALEAELALTLKVLEATADTDPALGDVLDQPLHTLHHILSQLRACIQPQPTAGPRTRG

RLHHWLHRLQEAPKKESPGCLEASVTFNLFRLLTRDLNSVASGDLSV

SEQ ID NO 4:
MVPVARLRGALPDARGCHIAQFKSLSPQELQAFKRAKDALEESLLLKDSKCRSRLFPRTWD

LRQLQVRERPVALEAELALTLKVLEAAAGPALEDVLDQPLHTLHHILSQLQACIQPQPTA

GPRPRGRLHHWLHRLQEAPKKESAGCLEASVTFNLFRLLTRDLKYVADGNLSLRTSTHPES

T

SEQ ID NO 5:
MKPTTTGKGCHIGRFKSLSPQELASFKKARDALEESLKLKNWSCSSPVFPGNWDLRLLQVR

ERPVALEAELALTLKVLEAAAGPALEDVLDQPLHTLHHILSQLRACIQPQPTAGPRTRGRL

HHWLHRLQEAPKKESPGCLEASVTFNLFRLLTRDLNSVASGDLSV

SEQ TD NO 6:
MVPVARLRGALPDARGCHIAQFKSLSPQELQAFKRAKDALEESLLLKDSKCRSRLFPRTWD

LRQLQVRERPVALEAELALTLKVLEATADTDPALGDVLDQPLHTLHHILSQLQACIQPQPT

AGPRPRGRLHHWLHRLQEAPKKESAGCLEASVTFNLFRLLTRDLKYVADGNLSLRTSTHPE

ST

SEQ ID NO 7:
MKPTTTGKGCHIGRFKSLSPQELASFKKARDALEESLKLKNWSCSSPVFPGNWDLRLLQVR

ERPVALEAELALTLKVLEAAAGPALEDVLDQPLHTLHHILSQLQACIQPQPTAGPRPRGRLH

HWLHRLQEAPKKESPGCLEASVTFNLFRLLTRDLNSVASGDLSV

SEQ ID NO 8:
MVPVARLRGALPDARGCHIAQFKSLSPQELQAFKRAKDALEESLLLKDSKCRSRLFPRTWD

LRQLQVRERPVALEAELALTLKVLEATADTDPALGDVLDQPLHTLHHILSQLRACIQPQPTA

GPRTRGRLHHWLHRLQEAPKKESAGCLEASVTFNLFRLLTRDLKYVADGNLSLRTSTHPE

ST

SEQ ID NO 9:
MKPTTTGKGCHIGRFKSLSPQELASFKKARDALEESLKLKNWSCSSPVFPGNWDLRLLQVR

ERPVALEAELALTLKVLEAAAGPALEDVLDQPLHTLHHILSQLQACIQPQPTAGPRPRGRLH

HWLHRLQEAPKKESAGCLEASVTFNLFRLLTRDLNSVASGDLSV

SEQ ID NO 10:
MVPVARLRGALPDARGCHIAQFKSLSPQELQAFKRAKDALEESLLLKDSKCRSRLFPRTWD

LRQLQVRERPVALEAELALTLKVLEATADTDPALGDVLDQPLHTLHHILSQLRACIQPQPTA

GPRTRGRLHHWLHRLQEAPKKESPGCLEASVTFNLFRLLTRDLKYVADGNLSLRTSTHPE

ST

SEQ ID NO 11:
MKPTTTGKGCHIGRFKSLSPQELASFKKARDALEESLKLKNWSCSSPVFPGNWDLRLLQVR

ERPVALEAELALTLKVLEAAAGPALEDVLDQPLHTLHHILSQLQACIQPQPTAGPRTRGRL

HHWLHRLQEAPKKESPGCLEASVTFNLFRLLTRDLNSVASGDLSV

SEQ ID NO 12:
MKPTTTGKGCHIGRFKSLSPQELASFKKARDALEESLKLKNWSCSSPVFPGNWDLRLLQVR

ERPVALEAELALTLKVLEATADTDPALGDVLDQPLHTLHHILSQLRACIQPQPTAGPRTRG

RLHHWLHRLQEAPKKESAGCLEASVTFNLFRLLTRDLKYVADGNLSLRTSTHPEST

-continued

SEQ ID NO 13:
MKPTTTGKGCHIGRFKSLSPQELASFKKARDALEESLKLKNWSCSSPVFPGNWDLRLLQVR

ERPVALEAELALTLKVLEATADTDPALGDVLDQPLHTLHHILSQLRACIQPQPTAGPRTRG

RLHHWLHRLQEAPKKESPGCLEASVTFNLFRLLTRDLKYVADGNLSLRTSTHPEST

SEQ ID NO 14:
MKPTTTGKGCHIGRFKSLSPQELASFKKARDALEESLKLKNWSCSSPVFPGNWDLRLLQVR

ERPVALEAELALTLKVLEATADTDPALGDVLDQPLHTLHHILSQLRACIQPQPTAGPRTRG

RLHHWLHRLQEAPKKESAGCLEASVTFNLFRLLTRDLKYVADGNLCLRTSTHPEST

SEQ ID NO 15:
MKPTTTGKGCHIGRFKSLSPQELASFKKARDALEESLKLKNWSCSSPVFPGNWDLRLLQVR

ERPVALEAELALTLKVLEATADTDPALGDVLDQPLHTLHHILSQLRACIQPQPTAGPRTRG

RLHHWLHRLQEAPKKESPGCLEASVTFNLFRLLTRDLKYVADGNLCLRTSTHPEST

SEQ ID NO 16:
MKPTTTGKGCHIGQFKSLSPQELASFKKARDALEESLKLKNWSCSSPVFPGNWDLRQLQVR

ERPVALEAELALTLKVLEATADTDPALGDVLDQPLHTLHHILSQLRACIQPQPTAGPRTRG

RLHHWLHRLQEAPKKESAGCLEASVTFNLFRLLTRDLKYVAEGNLSLRTSTHPEST

SEQ ID NO 17:
MKPTTTGKGCHIGRFKSLSPQELASFKKARDALEESLKLKNWSCSSPVFPGNWDLRQLQVR

ERPVALEAELALTLKVLEATADTDPALGDVLDQPLHTLHHILSQLRACIQPQPTAGPRTRG

RLHHWLHRLQEAPKKESPGCLEASVTFNLFRLLTRDLNSVASGDLSV

SEQ ID NO 18:
MVPVARLRGALPDARGCHIAQFKSLSPQELQAFKRAKDALEESLLLKDSKCRSRLFPRTWD

LRQLQVRERPVALEAELALTLKVLEAAAGPALEDVLDQPLHTLHHILSQLQACIQPQPTA

GPRPRGRLHHWLHRLQEAPKKESPGCLEASVTFNLFRLLTRDLNSVASGDLSV

SEQ ID NO 19:
MVPVARLRGALPDARGCHIAQFKSLSPQELQAFKRAKDALEESLLLKDSKCRSRLFPRTWD

LRQLQVRERPVALEAELALTLKVLEAAAGPALEDVLDQPLHTLHHILSQLQACIQPQPTA

GPRPRGRLHHWLHRLQEAPKKESAGCLEASVTFNLFRLLTRDLNSVASGDLSV

---

What is claimed is:

1. A fusion polypeptide having a structure of formula I:

(S1)-(helix A)-(S2)-(helix C)-(S3)-(helix D)-(S4)-(helix E)-(S5)-(helix F)-(S6), wherein the fusion polypeptide exhibits at least 90% sequence homology to IL28B (SEQ ID NO: 2) or IL29 (SEQ ID NO: 1); and wherein:
  a. helix D comprises an amino acid sequence exhibiting at least 90% homology to a fragment having residues from about V98 to Q112 of IL28B (SEQ ID NO: 2) or from about V89 to Q103 of IL29 (SEQ ID NO: 1);
  b. helix E comprises an amino acid sequence exhibiting at least 90% homology to a fragment having residues from about R130 to E145 of IL28B (SEQ ID NO:2) or from about R121 to E136 of IL29 (SEQ ID NO: 1);
  c. each of S1, S2, S3, S4, S5 and S6 is independently a spacer sequence having between 1 to about 50 amino acid residues; and
wherein said fusion polypeptide is characterized in that:
  i. helix A comprises an amino acid sequence exhibiting at least 90% homology to a fragment having residues from about P20 to L37 of IL29 (SEQ ID NO: 1), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G148 to A170 of IL28B (SEQ ID NO: 2); or
  ii. helix A comprises an amino acid sequence exhibiting at least 90% homology to a fragment having residues from about P27 to L44 of IL28B (SEQ ID NO: 2), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G139 to A161 of IL29 (SEQ ID NO: 1); or
  iii. helix A comprises an amino acid sequence exhibiting at least 90% homology to a fragment having residues from about P20 to L37 of IL29 (SEQ ID NO: 1), helix C comprises an amino acid sequence exhibiting at least 95% homology to a fragment having residues from about R56 to A80 of IL29 (SEQ ID NO: 1), and helix F comprises an amino acid sequence exhibiting at least 95% homology to a fragment having residues from about G148 to A170 of IL28B (SEQ ID NO: 2); or
  iv. helix A comprises an amino acid sequence exhibiting at least 90% homology to a fragment having residues from about P20 to L37 of IL29 (SEQ ID NO: 1), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G139 to A161 of IL29 (SEQ ID NO: 1).

2. The fusion polypeptide of claim 1, wherein helix A is identical to a fragment having residues from about P27 to L44 of IL28B (SEQ ID NO: 2).

3. The fusion polypeptide of claim 1, wherein helix A is identical to a fragment having residues from about P20 to L37 of IL29 (SEQ ID NO: 1).

4. The fusion polypeptide of claim 1, wherein helix C is identical to a fragment having residues from about R63 to A87 of IL28B (SEQ ID NO: 2).

5. The fusion polypeptide of claim 1, wherein helix C is identical to a fragment having residues from about R56 to A80 of IL29 (SEQ ID NO: 1).

6. The fusion polypeptide of claim 1, wherein helix F is identical to a fragment having residues from about G148 to A170 of IL28B (SEQ ID NO: 2).

7. The fusion polypeptide of claim wherein helix F is identical to a fragment having residues from about G139 to A161 of IL29 (SEQ ID NO: 1).

8. The fusion polypeptide of claim 1, wherein the fusion polypeptide having a structure of formula I exhibits at least 95% sequence homology to IL28B (SEQ ID NO: 2) or IL29 (SEQ ID NO: 1).

9. The fusion polypeptide of claim 1, wherein the N-terminus of said fusion polypeptide is further modified by a polyethylene glycol (PEG).

10. A host cell expressing the fusion polypeptide of claim 1.

11. A vector comprising a polynucleotide encoding the fusion polypeptide of claim 1.

12. A pharmaceutical composition comprising at least one of the fusion polypeptides of claim 1 and a pharmaceutically acceptable excipient.

13. A method of producing the fusion polypeptide of claim 1, comprising expressing a vector comprising a polynucleotide encoding the fusion polypeptide of claim 1 in a cell under conditions suitable for protein expression, thereby producing said fusion polypeptide.

14. The fusion polypeptide of claim 1, wherein:
S1 comprises an amino acid sequence exhibiting more than 90% homology to a fragment having residues from about M1 to S26 of IL28B (SEQ ID NO: 2) or more than 95% homology to a fragment having residues from about M1 to S19 of IL29 (SEQ ID NO: 1);
S2 comprises an amino acid sequence exhibiting more than 90% homology to a fragment having residues from about L45 to W62 of IL28B (SEQ ID NO: 2) or from about K38 to L55 of IL29 (SEQ ID NO: 1);
S3 comprises an amino acid sequence exhibiting more than 85% homology to a fragment having residues from about T88 to D97 of IL28B (SEQ ID NO: 2) or from about A81 to D88 of IL29 (SEQ ID NO: 1);
S4 comprises an amino acid sequence exhibiting more than 90% homology to a fragment having residues from about L113 to G129 of IL28B (SEQ ID NO: 2) or from about L104 to G120 of IL29 (SEQ ID NO: 1);
S5 comprises an amino acid sequence exhibiting more than 95% homology to a fragment having residues from about S146 to P147 of IL28B (SEQ ID NO: 2) or from about S137 to A138 of IL29 (SEQ ID NO: 1); and
S6 comprises an amino acid sequence exhibiting more than 90% homology to a fragment having residues from about S171 to V176 of IL28B (SEQ ID NO: 2) or more than 80% homology to a fragment having residues from about D162 to T176 of IL29 (SEQ ID NO: 1).

15. The fusion polypeptide of claim 1, wherein the fusion polypeptide having a structure of formula I exhibits at least 95% sequence homology to IL28B (SEQ ID NO: 2) or IL29 (SEQ ID NO: 1).

16. The fusion polypeptide of claim 1, wherein the fusion polypeptide having a structure of formula I exhibits at least 97% sequence homology to IL28B (SEQ ID NO: 2) or IL29 (SEQ ID NO: 1).

17. The fusion polypeptide of claim 1, wherein helix A comprises an amino acid sequence exhibiting at least 90% homology to a fragment having residues from about P20 to L37 of IL29 (SEQ ID NO: 1), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G148 to A170 of IL28B (SEQ ID NO: 2).

18. The fusion polypeptide of claim 1, wherein helix A comprises an amino acid sequence exhibiting at least 90% homology to a fragment having residues from about P27 to L44 of IL28B (SEQ ID NO: 2), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G139 to A161 of IL29 (SEQ ID NO: 1).

19. The fusion polypeptide of claim 1, wherein helix A comprises an amino acid sequence exhibiting at least 90% homology to a fragment having residues from about P20 to L37 of IL29 (SEQ ID NO: 1), helix C comprises an amino acid sequence exhibiting at least 95% homology to a fragment having residues from about R56 to A80 of IL29 (SEQ ID NO: 1), and helix F comprises an amino acid sequence exhibiting at least 95% homology to a fragment having residues from about G148 to A170 of IL28B (SEQ ID NO: 2).

20. The fusion polypeptide of claim 1, wherein helix A comprises an amino acid sequence exhibiting at least 90% homology to a fragment having residues from about P20 to L37 of IL29 (SEQ ID NO: 1), helix C comprises an amino acid sequence exhibiting at least 95% homology to a fragment having residues from about R63 to A87 of IL28B (SEQ ID NO: 2), and helix F comprises an amino acid sequence exhibiting at least 95% homology to a fragment having residues from about G139 to A161 of IL29 (SEQ ID NO: 1).

21. A fusion polypeptide comprising an amino acid sequence selected from the group consisting of SEQ ID NO:3, SEQ ID NO:5, SEQ ID NO:7, SEQ ID NO:9, SEQ ID NO:11, and SEQ ID NO:17.

22. A fusion polypeptide comprising an amino acid sequence selected from the group consisting of SEQ ID NO:11, SEQ ID NO:12, and SEQ ID NO:16.

23. A method of treating an infection by hepatitis B virus, hepatitis C virus and influenza virus in a mammal in need thereof, comprising administering to said mammal a therapeutically effective amount of the fusion polypeptide of claim 1.

24. A method of treating inflammation in a mammal in need thereof, comprising administering to said mammal a therapeutically effective amount of the fusion polypeptide of claim 1.

\* \* \* \* \*